US008409590B2

(12) United States Patent
Wimer-Mackin

(10) Patent No.: US 8,409,590 B2

(45) Date of Patent: Apr. 2, 2013

(54) ANTHRAX ANTIGENS AND METHODS OF USE

(75) Inventor: Susan Wimer-Mackin, Bozeman, MT (US)

(73) Assignee: Ligocyte Pharmaceuticals, Inc., Bozeman, MT (US)

(*) Notice: Subject to any disclaimer, the term of this patent is extended or adjusted under 35 U.S.C. 154(b) by 935 days.

(21) Appl. No.: 10/589,290

(22) PCT Filed: Feb. 11, 2005

(86) PCT No.: PCT/US2005/004678

§ 371 (c)(1), (2), (4) Date: Aug. 11, 2006

(87) PCT Pub. No.: WO2005/086637

PCT Pub. Date: Sep. 22, 2005

(65) Prior Publication Data

US 2007/0202130 A1 Aug. 30, 2007

Related U.S. Application Data

(60) Provisional application No. 60/544,130, filed on Feb. 11, 2004, provisional application No. 60/544,848, filed on Feb. 12, 2004.

(51) Int. Cl.
*A61K 39/07* (2006.01)

(52) U.S. Cl. ...................... 424/246.1; 424/489; 424/499

(58) Field of Classification Search ........................ None
See application file for complete search history.

(56) References Cited

U.S. PATENT DOCUMENTS

| | | | | |
|---|---|---|---|---|
| 4,172,126 | A | 10/1979 | Okonogi et al. | |
| 4,436,727 | A | 3/1984 | Ribi | |
| 4,436,728 | A | 3/1984 | Ribi et al. | |
| 4,912,094 | A | 3/1990 | Myers et al. | |
| 5,674,908 | A | 10/1997 | Haces et al. | |
| 5,962,428 | A | 10/1999 | Carrano et al. | |
| 6,197,755 | B1 | 3/2001 | Carrano et al. | |
| 6,329,156 | B1 | 12/2001 | Cirino et al. | |
| 6,348,450 | B1 | 2/2002 | Tang et al. | |
| 6,387,665 | B1 | 5/2002 | Farchaus et al. | |
| 6,592,872 | B1 | 7/2003 | Klimpel et al. | |
| 6,602,510 | B1 | 8/2003 | Fikes et al. | |
| 6,770,479 | B1 | 8/2004 | Lee et al. | |
| 6,979,449 | B1 | 12/2005 | Mock | |
| 7,354,760 | B2 * | 4/2008 | Daniell | 435/320.1 |
| 2002/0197272 | A1 * | 12/2002 | Galloway et al. | 424/190.1 |
| 2003/0118591 | A1 | 6/2003 | Levy | |
| 2003/0198651 | A1 | 10/2003 | Klimpel et al. | |
| 2006/0134143 | A1 * | 6/2006 | Schneerson et al. | 424/246.1 |

FOREIGN PATENT DOCUMENTS

| | | | |
|---|---|---|---|
| AU | 758019 | | 3/2003 |
| RU | 1789218 | A1 | 1/1993 |
| RU | 1566532 | C | 12/1995 |
| RU | 2056861 | CI | 3/1996 |
| RU | 2095409 | C1 | 11/1997 |
| RU | 2112544 | CI | 6/1998 |
| RU | 2115433 | CI | 7/1998 |
| RU | 2123532 | C1 | 12/1998 |
| RU | 2141340 | C1 | 11/1999 |
| RU | 2142009 | C1 | 11/1999 |
| RU | 2142010 | C1 | 11/1999 |
| RU | 2151798 | C1 | 6/2000 |
| RU | 2180917 | C1 | 3/2002 |
| RU | 2181294 | C2 | 4/2002 |
| RU | 2181296 | C2 | 4/2002 |
| RU | 2191599 | C1 | 10/2002 |
| RU | 2198921 | C2 | 2/2003 |
| WO | WO 98/11914 | A1 | 3/1998 |
| WO | WO 00/02522 | A2 | 1/2000 |
| WO | WO 01/19395 | A1 | 3/2001 |
| WO | WO 01/45639 | A2 | 6/2001 |
| WO | WO 02/055133 | A2 | 7/2002 |
| WO | WO 03/037370 | A2 | 5/2003 |
| WO | WO 03/048390 | A1 | 6/2003 |
| WO | WO 03/049670 | A2 | 6/2003 |
| WO | WO 2004/004654 | A2 | 1/2004 |
| WO | WO 2004/073735 | A1 | 2/2004 |
| WO | WO 2005/000884 | A1 | 1/2005 |
| WO | WO 2005/007804 | A2 | 1/2005 |
| WO | WO 2005/048918 | A2 | 6/2005 |
| WO | WO 2005/068493 | A1 | 7/2005 |

OTHER PUBLICATIONS

Greenspan et al. (Nature Biotechnology 7: 936-937, 1999).*

Greenbaum et al, Journal of Molecular Recognition, 20(2):75-82, 2007.*

Blythe et al, Protein Science 14:246-248, 2005.*

Alper et al , In:MVADS Conference Jun. 4-6, 2003, Dublin, Republic of Ireland.*

Sigma Chemical Catalog 2002-2003, p. 86, MPL+TDM emulsion.*

Boyaka et al., "Effective Mucosal Immunity to Anthrax: Neutralizing Antibodies and Th Cell Responses Following Nasal Immunization with Protective Antigen," *J. Immunol.* 170:5636-5643 (2003).

Chabot et al., "Anthrax capsule vaccine protects against experimental infection," *Vaccine* 23:43-47 (2004).

Daubenspeck et al., "Novel Oligosaccharide Side Chains of the Collagen-like Region of Bc1A, the Major Glycoprotein of the *Bacillus anthracis* Exosporium," *J. Biol. Chem.* 279:30945-30953 (2004).

Flick-Smith et al., "Mucosal or Parenteral Administration of Microsphere-Associated *Bacillus anthracis* Protective Antigen Protects against Anthrax Infection in Mice," *Infect. Immunity* 70:2022-2028 (2002).

Gaur et al., "Effect of nasal immunization with protective antigen of *Bacillus anthracis* on protective immune response against anthrax toxin," *Vaccine* 20:2836-2839 (2002).

Ivins et al., "Comparative efficacy of experimental anthrax vaccine candidates against inhalation anthrax in rhesus macaques," *Vaccine* 16:1141-1148 (1998).

(Continued)

*Primary Examiner* — Patricia A Duffy

(74) *Attorney, Agent, or Firm* — Cooley LLP

(57) ABSTRACT

Anthrax antigens are provided that find use as immunogens and vaccines.

16 Claims, 10 Drawing Sheets

OTHER PUBLICATIONS

Kozel et al., "mAbs to *Bacillus anthracis* capsular antigen for immunoprotection in anthrax and detection of antigenemia," *Proc. Natl. Acad. Sci. USA* 101:5042-5047 (2004).

LaForce, "Anthrax," *Clin. Infect. Dis.* 19:1009-1014 (1994).

Mikszta et al., "Protective Immunization against Inhalational Anthrax : A Comparison of Minimally Invasive Delivery Platforms," *J. Infect. Dis.* 191:278-288 (2005).

Reynolds, "Modulating airway defenses against microbes," *Curr. Opin. Pulmonary Med.* 8: 1 page abstract (2002).

Rhie et al., "A dually active anthrax vaccine that confers protection against both bacilli and toxins," *Proc. Natl. Acad. Sci. USA* 100:10925-10930 (2003).

Schneerson et al., "Poly(γ-D-glutamic acid) protein conjugates induce IgG antibodies in mice to the capsule of *Bacillus anthracis*: A potential addition to the anthrax vaccine," *Proc. Natl. Acad. Sci. USA* 100:8945-8950 (2003).

Sigma-Aldrich, "MPL® +TDM Adjuvant System," 2 pages, Sigma-Aldrich, 2002.

Sylvestre et al., "Polymorphism in the Collagen-Like Region of the *Bacillus anthracis* BclA Protein Leads to Variation in Exosporium Filament Length," *J Bacteriol.* 185:1555-1563 (2003).

Sylvestre et al., "A collagen-like surface glycoprotein is a structural component of the *Bacillus anthracis* exosporium" *Mol. Microbiol.* 45:169-178 (2002).

Wimer-Mackin et al., "An intranasal vaccine targeting both the *Bacillus anthracis* toxin and bacterium provides protection against aerosol spore challenge in rabbits," *Vaccine* 24:3953-3963 (2006).

Ivins el al., "Experimental anthrax vaccines: efficacy of adjuvants combined with protective antigen against an aerosol *Bacillus anthracis* spore challenge in guinea pigs", Vaccine, vol. 13: 1779-1784, Dec. 1995.

Ivins et al., "Immunization against anthrax with *Bacillus anthracis* protective antigen combined with adjuvants", Infection and Immunity, vol. 60: 662-668, Feb. 1992.

European Supplementary Partial Search Report for related European Patent Application No. 05758632, Mar. 10, 2008.

International Search Report dated Oct. 18, 2006 for corresponding application No. PCT/US05/04678.

Van Der Lubben et al. "Chitosan for mucosal vaccination" Advanced Drug Delivery Reviews, vol. 52:139-144, 2001.

Huang et al. "A novel dry powder influenza vaccine and intranasal delivery technology: induction of systemic and mucosal responses in rats," Vaccine, vol. 23: 794-801, 2004.

* cited by examiner

SEQUENCE LISTING

```
<160> NUMBER OF SEQ ID NOS: 3

<210> SEQ ID NO 1
<211> LENGTH: 10
<212> TYPE: PRT
<213> ORGANISM: Artificial Sequence
<220> FEATURE:
<223> OTHER INFORMATION: Poly (gamma-D glutamic acid) 10-mer peptide
<220> FEATURE:
<221> NAME/KEY: MISC_FEATURE
<222> LOCATION: (1)..(1)
<223> OTHER INFORMATION: May be conjugated to a linker peptide
<220> FEATURE:
<221> NAME/KEY: MISC_FEATURE
<222> LOCATION: (1)..(9)
<223> OTHER INFORMATION: Gamma D-glutamate
<220> FEATURE:
<221> NAME/KEY: MISC_FEATURE
<222> LOCATION: (10)..(10)
<223> OTHER INFORMATION: D-glutamate

<400> SEQUENCE: 1

Glu Glu Glu Glu Glu Glu Glu Glu Glu Glu
1               5                   10


<210> SEQ ID NO 2
<211> LENGTH: 13
<212> TYPE: PRT
<213> ORGANISM: Artificial Sequence
<220> FEATURE:
<223> OTHER INFORMATION: Linked 9-mer peptide representing B. anthracis
      capsule
<220> FEATURE:
<221> NAME/KEY: MISC_FEATURE
<222> LOCATION: (1)..(1)
<223> OTHER INFORMATION: May be acetylated
<220> FEATURE:
<221> NAME/KEY: MISC_FEATURE
<222> LOCATION: (5)..(12)
<223> OTHER INFORMATION: Gamma D-glutamate
<220> FEATURE:
<221> NAME/KEY: MISC_FEATURE
<222> LOCATION: (12)..(12)
<223> OTHER INFORMATION: D-glutamate

<400> SEQUENCE: 2

Cys Gly Gly Gly Glu Glu Glu Glu Glu Glu Glu Glu Glu
1               5                   10


<210> SEQ ID NO 3
<211> LENGTH: 4
<212> TYPE: PRT
<213> ORGANISM: Artificial Sequence
<220> FEATURE:
```

-continued

```
<223> OTHER INFORMATION: Peptide linker sequence
<220> FEATURE:
<221> NAME/KEY: MISC_FEATURE
<222> LOCATION: (1)..(1)
<223> OTHER INFORMATION: May be acetylated

<400> SEQUENCE: 3

Cys Gly Gly Gly
1
```

ANTHRAX ANTIGENS AND METHODS OF USE

This application is a national stage filing of PCT/US2005/004678, filed Feb. 11, 2005, which claims the benefit of the filing dates of U.S. Application Ser. No. 60/544,130, filed Feb. 11, 2004, and U.S. Application Ser. No. 60/544,848, filed Feb. 12, 2004. All these applications are herein incorporated by reference.

STATEMENT OF GOVERNMENT SUPPORT

This invention was made with government support under DOD contract DAMD17-01-C-0040. The US Government may have certain rights in the invention as a result of this support.

INTRODUCTION

Anthrax is a lethal infectious disease caused by *Bacillus anthracis*, a spore-forming, gram-positive bacterium. In its most contagious and lethal form, pulmonary or inhalation anthrax, anthrax spores (endospores) are inhaled and germinate in alveolar macrophages. The macrophages transport the bacterium from the lungs to the host circulatory system. Once released from the macrophages, *B. anthracis* replicates extracellularly, causing flu-like symptoms followed by massive hypotension and pulmonary edema. (Demicheli et al. Vaccine 16:880-884 (1998); Friedlander. J. Appl. Microbiol. 87:303 (1999); Hambleton et al. 1984. Vaccine 2:125-132 (1984); Jernigan et al. Emerg. Infect. Dis. 7:933-944 (2001))

Two major *B. anthracis* virulence factors are plasmids, pXO1 and pXO2. (Okinaka et al. Sequence and organization of pXO1, the large *Bacillus anthracis* plasmid harboring the anthrax toxin genes J. Bacteriol. 181(20):6509-6515 (1999); Okinaka et al. Sequence, assembly and analysis of pX01 and pX02. J. Appl. Microbiol. 87(2):261-262 (1999)) pXO2 encodes poly-γ-D-glutamic acid (PGA), which is a major component of the bacterium's capsule. PGA is weakly immunogenic and possesses antiphagocytic properties, i.e., unencapsulated strains are readily phagocytized and virtually avirulent. pXO1 encodes the protein subunits of the secreted exotoxins, lethal toxin (LeTx) and Edema Toxin (EdTx). Each exotoxin contains A and B subunits. The A subunit of EdTx is edema factor (EFa), an adenyl cyclase. The A subunit of LeTx is lethal factor (LFa), a metalloproteinase. The B subunit of both exotoxins is protective antigen (PA), which is a binding partner of the toxins' cellular receptor. In the presence of furin-like proteases, a 20 kDa piece is removed from the full length PA molecule (83 kDa), forming $PA_{63}$ (63 kDa). $PA_{63}$ interacts with other $PA_{63}$ molecules to form heptamer(s) ($PA_7$) and also interacts with LFa and/or EFa to form LeTx and EdTx, respectively.

The current human anthrax vaccine is an aluminum hydroxide-adsorbed supernatant from fermentor cultures of a toxigenic, non-encapsulated strain of *B. anthracis* V770-NPI-R (Anthrax Vaccine Adsorbed (AVA)). The vaccine is expensive to produce, requires repeated immunizations, and causes local pain with edema and erythema. The course of immunization consists of three subcutaneous injections 2 weeks apart, three injections 6 months apart, and an annual injection as long as the subject remains at risk. Recent events have demonstrated the potential of anthrax as a bioweapon and the susceptibility of large segments of the civilian population. (Friedlander et al. J. Infect. Dis. 167:1239-1243 (1993)). The disadvantages of the current vaccine make it unfeasible for widespread administration before or after a bioterrorist attack. (Institute of Medicine. 2002. The Anthrax Vaccine. Is It safe? Does It Work? National Academy Press, Washington, D.C.)

Thus, there is a need for an effective anthrax vaccine that is a suitable therapeutic and prophylactic. To this end, the present invention provides anthrax vaccines that target one or more of the bacterium's major virulence factors, immune avoidance factors, and other targets related to pathogenicity. The vaccines can be formulated for administration at a mucosal surface to provide immunity at the routes of entry of the most lethal and contagious forms of the disease.

SUMMARY

This invention relates generally to anthrax peptides that induce an immune response to anthrax when administered to a subject. In some embodiments, the invention provides methods of inducing an immune response to anthrax by administering one or more anthrax peptides formulated with an adjuvant to a mucosal surface of a subject. In various exemplary embodiments, the immune response induced by anthrax peptides can ameliorate and/or prevent at least one symptom of anthrax disease. In some embodiments, the immune response induced by anthrax peptides can ameliorate and/or prevent anthrax disease. Therefore, the compositions disclosed herein find use as immunogens, including but not limited to, vaccines and therapeutic agents.

In some embodiments, the invention provides a composition comprising an anthrax peptide and an adjuvant.

In a preferred embodiment, the invention provides the composition comprising an anthrax peptide of LeTx and/or EdTx, such as, PA, LF, EF, and/or immunogenic fragments thereof. In a preferred embodiment, the composition comprises an anthrax peptide of PGA or immunogenic fragments thereof. In a preferred embodiment, the compositions comprise an anthrax peptide of BclA or immunogenic fragments thereof. In a preferred embodiment, the composition comprises a combination of two or more anthrax peptides and/or immunogenic fragments thereof.

In some embodiments, an adjuvant can be a mucosal adjuvant. In some embodiments, a mucosal adjuvant can be an invasin protein of a gram-negative bacterium, including but not limited to, a *Shigella* or *Escherichia* invasin protein. In a preferred embodiment, a mucosal adjuvant can be an immunogenic component of a gram-negative bacterial cell wall, including but not limited to, lipid A. In a preferred embodiment, a mucosal adjuvant can be an agonist of a toll-like receptor (e.g., TLR4). In a preferred embodiment, a mucosal adjuvant can be signaling transducer receptor of lipopolysaccharide (LPS). In a preferred embodiment, a mucosal adjuvant can stimulate innate immunity. In a preferred embodiment a mucosal adjuvant can be monophosphoryl lipid A (MPL). In a preferred embodiment, a mucosal adjuvant can be synthetic trehalose dicorynomycolate (TDM). In a preferred embodiment, a mucosal adjuvant can be a positively charged linear polysaccharide, for example, chitosan, which is derived from the shells of crustaceans and is suitable for acting as a depot. In a preferred embodiment, a mucosal adjuvant can be a combination of two or more mucosal adjuvants.

In other aspects, the invention provides methods of inducing an immune response to anthrax bacterium comprising administering a composition of the invention to a subject. In some embodiments, an immune response to anthrax bacterium can be induced by administering an anthrax peptide to a subject. In a preferred embodiment, the immune response can be to a LeTx, EdTx, BclA and/or PGA and/or immunogenic fragments thereof. The immune response that can be induced protects and/or ameliorates anthrax disease in a subject and therefore does not cause anthrax disease or exacerbate a disease symptom. Thus, in some embodiments the invention provides methods of protecting a subject from anthrax disease. In some embodiments, the invention provides methods of preventing anthrax bacterium from producing at least one disease symptom in a subject. In some embodiments, the invention provides methods of ameliorating at least one symptom of anthrax disease in a subject.

In another aspect, the invention provides antibodies that find use as anthrax immunotherapeutics.

These and other features of the present disclosure are set forth herein.

BRIEF DESCRIPTION OF THE DRAWINGS

The skilled artisan will appreciate that the drawings and accompanying descriptions, below, are for illustration purposes only and therefore are not intended to limit the scope of the present disclosure in any way.

DETAILED DESCRIPTION OF VARIOUS EMBODIMENTS

Figure 1:
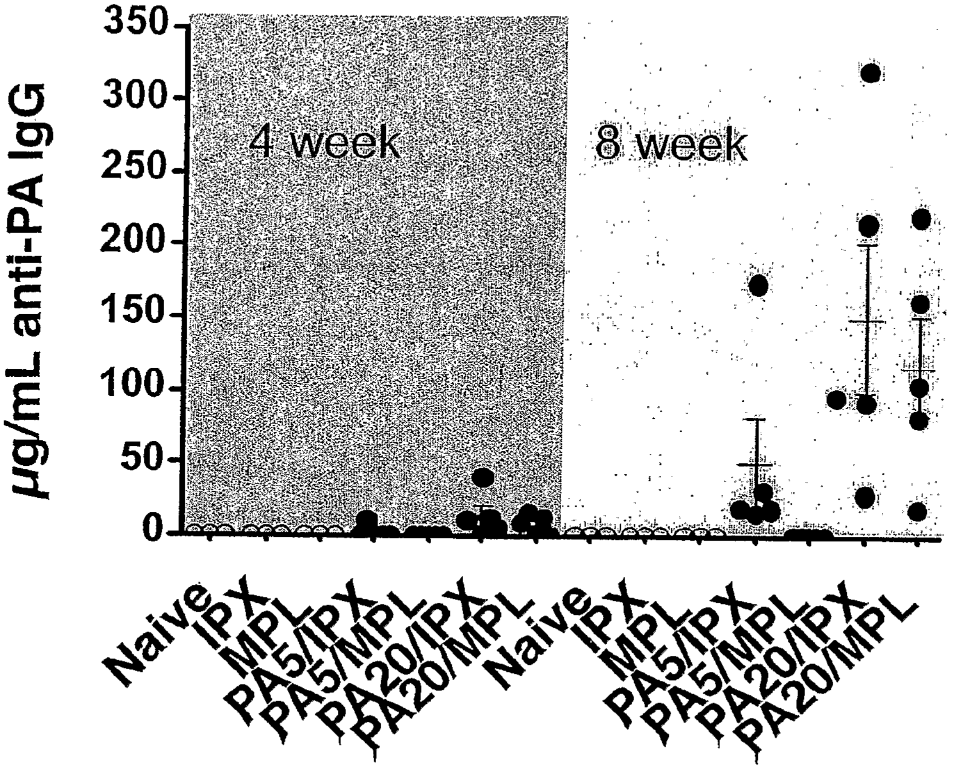
FIG. 1 shows ELISA results for sera collected at 4 weeks (Left) and 8 weeks (Right) following initial vaccination (Example 1). The value of each individual mouse is indicated by a circle. Mean values for each treatment ±standard error of the mean are indicated by bars. The PA content of immunizations is indicated in the horizontal axis labels.

In this application, the use of the singular includes the plural unless specifically stated otherwise. The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The present invention is directed to the discovery that certain anthrax antigens administered to a mucosal surface of a subject induce an immune response to anthrax and do not substantially induce, cause, and/or exacerbate anthrax disease. Thus, anthrax antigens disclosed herein find use as therapeutics and preventative treatments of anthrax disease.

In addition to compositions, the present invention provides methods of inducing an immune response to anthrax by inducing an immune response to anthrax antigens. The immune response induced by the anthrax antigens reacts with the etiologic agent of anthrax disease and/or an anthrax virulence factor, thereby treating or preventing one or more disease symptoms.

In some embodiments, the methods comprise inducing an immune response to an anthrax peptide, which as disclosed herein includes immunogenic fragments thereof. The immune response can be induced by administering an anthrax peptide and/or immunogenic fragments formulated with a mucosal adjuvant to a mucosal surface of a subject. The anthrax peptide preferably can be a LeTx, EdTx, PGA, or BclA peptide, immunogenic peptide fragments or combinations thereof. Preferably the immune response protects the subject from anthrax disease or ameliorates a disease symptom.

Accordingly, the present invention provides compositions comprising one or more anthrax peptides and an adjuvant that can induce an immune response to anthrax. By "immune response to anthrax" and grammatical equivalents as used herein refer to an immune response that is capable of reacting with at least one virulence factor of anthrax disease and/or an organisms that produces or is capable of producing at least one virulence factor of anthrax disease. Thus, "anthrax" as used herein refers to a virulence factor of anthrax disease and the causative organism of anthrax disease. "Capable of producing at least one virulence factor of anthrax disease" as used herein refers to an organism that can produce or can be modified to produce at least one virulence factor of anthrax disease. An organism that can produce or can be modified to produce at least one virulence factor of anthrax disease includes but is not limited to a "wild-type" organism or a genetically altered organism that can produce one or more anthrax virulence factors. For example, in some embodiments, an organism can be genetically altered by the introduction and expression of pXO1 and/or pXO2 sequences.

Therefore, in some embodiments, "immune response to anthrax" can be an immune response to a vegetative, gram-positive, rod-shaped bacterium, *B. anthracis*. In some embodiments, an "immune response to an anthrax" can be an immune response to a non-vegetative, spore of *B. anthracis. In some embodiments, an "immune response to an anthrax" can be an immune response to an anthrax virulence factor, including but not limited to LeTx, EdTx, and/or PGA. In some embodiments, an immune response can confer immunity to a subject.*

"Immune system" and grammatical equivalents herein refer a system of cellular and molecular components that can function to distinguish self from non-self and function as a defense against transformed cells (e.g., benign and malignant tumors, cancer cells and the like), foreign organisms, and substances. The components of the immune system can include cells, such as, leukocytes, lymphocytes (e.g., T-cell (e.g. Th1, Th2, TR1. $T_K$, NK cells), B-cells), macrophages, antigen presenting cells (APC), granulocytes (e.g., neutrophils, eosinophils, basophils, mast cells), monocytes, dendritic cells, M cells, epithelium (e.g., surface epithelium), and the like. Components of the immune system can include secreted molecules, such as, immunoglobulin (antibody, e.g., IgA, secretory IgA, IgM, IgG, IgE and the like), cytokines (e.g., Type I cytokines, interferons (Type II cytokines), interleukins, chemokines, and the like), tumor necrosis factors (e.g. TNF 1-19), the complement system, lysozyme, chitinases, phospholipase (e.g., phospholipase A2), bactericidal permeability-increasing protein (BPI), defensins, cathelicidins, serprocedins, lactoferrin and the like (see, e.g., Fundamental Immunology 1-1701 (Paul, ed., 5th ed., Lippincott Williams & Wilkins 2003 (ISBN 0-7817-3514-9))). Other components of the immune system can include, but are not limited to, major histocompatibility antigens, T-cell receptors, B-cell receptors, CD antigens, pattern recognition receptors (PRRs), secreted pattern recognition receptors (PRMs), toll-like receptors (TLRs, e.g., TLR1, 2, 3, 4, 5, 6, 7, 8, 9, 10), and the like. (Fundamental Immunology 1-1701 (Paul, ed., 5th ed., Lippincott Williams & Wilkins 2003 (ISBN 0-7817-3514-9)); Goodman and Gilman's The Pharmacological Basis of Therapeutics 1463-1486 (Hardman et al., ed., 10th ed., McGraw-Hill 2001 (ISBN 0-07-112432-2)))

The skilled artisan will appreciate that the immune system generally is capable of producing an innate immune response and an adaptive immune response. (Fundamental Immunology 497-523, 561-565, 816-819 (Paul, ed., 5th ed., Lippincott Williams & Wilkins 2003 (ISBN 0-7817-3514-9)); Goodman and Gilman's The Pharmacological Basis of Therapeutics 1463-1486 (Hardman et al., ed., 10th ed., McGraw-Hill 2001 (ISBN 0-07-112432-2)); Roitt et al. Immunology 1.1-1.10, 2.8, 9.1-9.13, 13.3, 15.1-15.9, 18.6-18.8, 16.2-16.5 (2d ed. Gower Medical Publishing 1989)) An innate immune response generally can be characterized as not being substantially antigen specific and/or not generating immune memory. (Fundamental Immunology 497-518 (Paul, ed., 5th ed., Lippincott Williams & Wilkins 2003 (ISBN 0-7817-3514-9)); Goodman and Gilman's The Pharmacological Basis of Therapeutics 1463-1486 (Hardman et al., ed., 10th ed., McGraw-Hill 2001 (ISBN 0-07-112432-2)); Roitt et al. Immunology 1.1-1.10 (2d ed. Gower Medical Publishing 1989)) In contrast, an adaptive immune response can be characterized as being substantially antigen specific, maturing over time (e.g., increasing affinity and/or avidity for antigen), and in general can produce immunologic memory. Even though these and other functional distinctions between innate and adaptive immunity can be discerned, the skilled artisan will appreciate that the innate and adaptive immune systems can be integrated and therefore can act in concert. (Fundamental Immunology 512-513 (Paul, ed., 5th ed., Lippincott Williams & Wilkins 2003 (ISBN 0-7817-3514-9)); Goodman and Gilman's The Pharmacological Basis of Therapeutics 1463-1486 (Hardman et al., ed., 10th ed., McGraw-Hill 2001 (ISBN 0-07-112432-2)); Roitt et al. Immunology 1.10 (2d ed. Gower Medical Publishing 1989)) Therefore, the induction of an innate immune response can lead to an adaptive immune response and vice versa.

"Immune response" as used herein refers to a response of the immune system to one or more anthrax antigens. In various exemplary embodiments, an immune response to an anthrax antigen can be an innate and/or adaptive response. In some embodiments, an adaptive immune response can be a "primary immune response" which as used herein refers to an immune response occurring on the first exposure of a "naïve" subject to an antigen. For example, in the case of a primary antibody response, after a lag or latent period of from approximately 3 to 14 days depending on, for example, the antigen, dose, and subject, antibodies to an anthrax antigen can be produced. Generally, IgM production lasts for several days followed by IgG production and the IgM response can decrease. Antibody production can terminate after several weeks but memory cells can be produced. In some embodiments, an adaptive immune response can be a "secondary immune response", "anamnestic response," or "booster response" which as used herein refer to the immune response occurring on a second and subsequent exposure of a subject to an antigen. Generally, in a secondary immune response, memory cells respond to the antigen and therefore the secondary immune response can differ from a primary immune response qualitatively and/or quantitatively. For example, in comparison to a primary antibody response, the lag period of a secondary antibody response can be shorter, the peak antibody titer can be higher, higher affinity antibody can be produced, and/or antibody can persist for a greater period of time.

In some embodiments, an immune response to an anthrax antigen can react with anthrax. Thus, the skilled artisan will appreciate that in some embodiments, an immune response to an anthrax antigen can react with the causative agent of anthrax disease and/or a virulence factor of anthrax disease. In various exemplary embodiments, an immune response to an anthrax antigen can substantially prevent, reduce, inhibit, neutralize and/or inactivate a symptom of anthrax disease. Therefore, in some embodiments, an immune response to an anthrax antigen can ameliorate anthrax disease. In a preferred embodiment, an immune response to an anthrax antigen can be a protective immune response. "Protective immune response" as used herein is a response that provides immunity to anthrax.

"Anthrax antigen" as used herein refers to an antigen suitable for inducing an immune response to anthrax that does not induce or exacerbate a symptom of anthrax disease in a subject. Thus, anthrax antigens find use in the treatment of anthrax. In various exemplary embodiments, an anthrax antigen can be an antigen of an anthrax spore (e.g., BclA), an antigen of a vegetative bacterium (e.g., a cell wall antigen, capsule antigen (e.g., PGA), secreted antigen (e.g., exotoxin). In some embodiments, an anthrax antigen can be an anthrax peptide, including immunogenic fragments thereof. In various exemplary embodiments, an anthrax peptide can be an anthrax exotoxin peptide (e.g., EF, LF, $LF_n$, PA, $PA_{63}$), PGA, BclA, peptide fragments, and combinations thereof. "Peptide", "polypeptide", "oligopeptide" and "protein" are used interchangeably herein and refer to a polymer of at least two covalently attached amino acid residues. "Amino acid" as used herein refers to a molecule containing amino and carboxylic acid groups and therefore includes but is not limited to α-, β-, γ-amino acids and so on, imino acids (e.g., proline, hydroxyproline, histidine) and the like. "Amino acid residue" and "peptide residue" as used herein refer to what remains of an amino acid after an amino acid is covalently attached via a peptide bond.

"Amino acid", "amino acid residue", and "peptide residue" as used herein include molecules having naturally occurring and synthetic structures (e.g., naturally occurring amino acids, amino acid analogs, peptide bonds, synthetic peptidomimetic structures (e.g., "peptoids" (see Simon et al., PNAS USA 89(20):9367 (1992)), γ-linkages, homophenylalanine, citrulline, noreleucine). One or more side chains may be in either the (R) or the (S) configuration. In a preferred embodiment, all side chains are in the (S) or L-configuration. In a preferred embodiment, the side chains are in a configuration suitable for inducing an immune response that reacts with anthrax. In some embodiments, non-amino acid substituents can be attached to a peptide, for example, to prevent or retard in vivo degradation. A peptide that includes a non-naturally occurring side chain and/or other structure may be synthesized or in some cases, made recombinantly. (Hest et al. FEBS Lett. 428(1-2):68-70 (1998), Tang et al., Abstr. Pap. Am. Chem. S218:U138 Part 2 Aug. 22, 1999)

"Anthrax peptide" includes but is not limited to peptides comprising the full length sequence of the naturally occurring peptide and peptides that can be shorter or longer than the naturally occurring amino acid sequences encoded by an anthrax bacterium or its plasmids, pXO1 or pXO2. In various exemplary embodiments, an anthrax peptide comprises one or more of the following: a) the ability to block binding of an antibody to anthrax; b) the ability to block binding of an anthrax peptide to a host cell or to another anthrax peptide; c) the ability to induce antibody cross-reactive with anthrax; d) at least one biological activity of a naturally-occurring anthrax peptide; e) at least the homology described herein; f) the ability to induce an immune response to anthrax; or g) the ability to induce a protective or therapeutic immune response to anthrax disease. In some embodiments, an anthrax peptide exhibits two or more of these characteristics. In some embodiments, an anthrax peptide that share at least one antigenic epitope with a naturally-occurring protein.

Thus, "anthrax peptide" as used herein includes a peptide having a sequence homologous or identical to an amino acid sequence of a naturally occurring anthrax peptide. Thus, anthrax peptide includes recombinantly expressed, and/or isolated and/or purified, and/or synthetic peptides. In some embodiments, an anthrax peptide can be a full length peptide as produced by an anthrax bacterium. In some embodiments, an anthrax peptide can be a fragment of a full-length peptide particularly for PA, LF, EF, PGA and BclA. By "fragment" and grammatical equivalents herein are meant a peptide that is at least one amino acid residue shorter in comparison to full length peptide. In various exemplary embodiments, an anthrax peptide can be about 5 to about 50 amino acids in length, from about 5 to about 30 amino acids in length, from about 5 to about 15 amino acids in length, and from 5 to about 10 amino acids in length. In some embodiments, an anthrax peptide can comprise about 1%, 5%, 10%, 15%, 20%, 25%, 30%, 35%, 40%, 45%, 50%, 55%, 60%, 65%, 70%, 75%, 80%, 85%, 90%, 95%, 99%, or 100% of the number of amino acids comprising a full length peptide.

In various exemplary embodiments, an anthrax peptide can comprise a sequence homologous to either the PA, LF, EF, PGA, and/or BclA peptides. (see the sequences shown in Okinaka et al. J. Bacteriol. 181(20):6509-6515 (1999); Okinaka et al. J. Appl. Microbiol. 87(2):261-262 (1999); and NCBI: AJ516947, AJ516946, AJ516945, AJ516944, AJ516943, for expressly incorporated by reference in their entirety. In various exemplary embodiments, the homology of an anthrax peptide sequence and the corresponding sequence of an anthrax bacterium can be greater than about 75%, greater than about 80%, greater than about 85%, greater than about 90%, greater than about 95%, or greater than about 98%. In some embodiments the homology can from about 93 to about 95 to about 98% to about 100%. "Homology" as used herein refers to sequence similarity or identity, with identity being preferred. Homology can be determined using standard techniques known in the art and described below.

In some embodiments, an "anthrax peptide" includes a peptide that induces an antibody that binds to an amino acid sequence deduced from an anthrax nucleic acid. Therefore, an anthrax peptide can comprise an epitope that induces an antibody in a subject that binds to an amino acid sequence deduced from an anthrax nucleic acid. As known in the art, antibodies recognize either linear or conformational epitopes. By "epitope", "antigenic determinant", and grammatical equivalents herein are meant a region of an antigen or immunogen that can be specifically recognized (i.e., binds to) a molecular component of an immune response that functions in immune recognition (e.g., antibody, T-cell receptor, B-cell receptor). "Linear epitope" herein refers to an epitope comprising a sequence of at least about 5, 6, 7, 8, 9, 10, 11, 12, 13, 14, 15, 16, 17, 18, 19, or about 20 amino acids connected in a linear fashion, which amino acids, by themselves or as part of a larger sequence, can induce an immune response and/or can be recognized by the immune system, including immune effector mechanisms, as known in the art. "Conformational epitope" herein refers to an epitope comprising amino acids whose three dimensional or tertiary structure, alone or as part of a larger sequence, can induce an immune response (e.g., antibody) and/or can be recognized by (e.g., binds to) the immune system. The skilled artisan will appreciate that generally but not uniformly, amino acids that comprise a conformational epitope do not comprise a continuous, linear sequence of amino acid residues within a protein's primary structure. In some embodiments, a conformational epitope can comprise amino acid residues from two more peptides. Therefore, in some embodiments a conformation epitope can be formed as a result of the molecular interactions that result in the formation of homo- or heterodimers and trimers and the like.

In some embodiments, an epitope can be substantially unique, e.g., an epitope can induce an immune response characterized by statistically insignificant or no detectable cross-reactivity with other epitopes and/or peptides.

In some embodiments, an epitope can induce an immune response characterized by statistically significant cross-reactivity with another epitope and/or peptide. Therefore, in some embodiments, an epitope can be shared by peptides having statistically insignificant homology in their linear amino acid sequences. For example, in some embodiments, a conformational epitope can be shared by peptides having non-homologous amino acid sequences because the tertiary structure of the peptides and a conformational epitope contained therein can be substantially similar.

When an anthrax peptide is used to generate antibodies that recognize anthrax, the anthrax peptide shares at least one epitope with a full length anthrax protein. Thus, in some embodiments, antibodies to an anthrax peptide that has an amino acid sequence that is shorter than the full length peptide can bind to the full length peptide.

Also included within the definition of anthrax peptides of the present invention are amino acid sequence variants. Anthrax peptide variants can fall into one or more classes, such as, substitutional, insertional or deletional variants. These variants ordinarily can be prepared by site specific mutagenesis of nucleotides in a DNA encoding an anthrax peptide, using cassette or PCR mutagenesis or other techniques well known in the art, to produce DNA encoding the variant, and thereafter expressing the DNA in recombinant cell culture or in vitro expression techniques as known in the art. However, variant anthrax peptides having up to about 100-150 residues may be prepared by in vitro synthesis using established techniques. Amino acid sequence variants are characterized by the predetermined nature of the variation, a feature that sets them apart from naturally occurring variation of an anthrax peptide amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed anthrax peptide variants screened for the optimal combination of desired activity. Techniques for making substitution mutations at predetermined sites in DNA having a known sequence are well known, for example, M13 primer mutagenesis and PCR mutagenesis. Screening of the mutants is done using assays of anthrax peptide activities, as known in the art.

Amino acid substitutions typically can be single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final variant. Generally these changes can be done on a few amino acids to minimize the alteration of the molecule. However, larger changes may be tolerated in certain circumstances. When small alterations in the characteristics of the anthrax peptide are desired, substitutions are generally made in accordance with the following chart:

CHART I

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity can be made by selecting substitutions that are less conservative than those shown in Chart I. For example, substitutions may be made which more significantly affect: the structure of the peptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, can be substituted for (or by) a hydrophobic residue, e.g. leucyl, isoleucyl, phenylalanyl, valyl or alanyl; (b) a cysteine or proline can be substituted for (or by) any other residue; (c) a residue having an electropositive side chain, e.g. lysyl, arginyl, or histidyl, can be substituted for (or by) an electronegative residue, e.g. glutamyl or aspartyl; or (d) a residue having a bulky side chain, e.g. phenylalanine, can be substituted for (or by) one not having a side chain, e.g. glycine.

The variants typically exhibit the same qualitative biological activity and elicit a substantially similar immune response as the naturally-occurring analogue, although variants can be selected to modify the characteristics of an anthrax peptide as needed. Alternatively, a variant may be designed such that the biological activity of the anthrax peptide is altered.

Covalent modifications of anthrax peptides are included within the scope of this invention, particularly for screening assays, therapeutic or prophylactic uses. One type of covalent modification includes reacting targeted amino acid residues of anthrax peptide with an organic derivatizing agent that is capable of reacting with selected side chains or the N- or C-terminal residues of an anthrax peptide. Derivatization with bifunctional agents can be useful, for instance, for crosslinking anthrax peptide to a water-insoluble support matrix or surface for use in the methods described below, or for in vivo stability. Commonly used crosslinking agents include but are not limited to, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate, and 1-ethyl-3-(−3-dimethylaminopropyl)carbodiimide hydrochloride.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the amino groups of lysine, arginine, and histidine side chains (see, e.g., T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

In addition, modifications such as derivitization with polyethylene glycols (and other glycols) to increase the in vivo stability half-life are also included.

In some embodiments, an anthrax peptide may be linked to adjuvants or other molecules to increase the immune response to the anthrax peptide. In some embodiments, a chimeric molecule comprises a fusion of an anthrax peptide with a tag polypeptide which in some embodiments can provide an epitope to which an anti-tag antibody can selectively bind. The epitope tag generally can be placed at the amino- or carboxyl-terminus of the anthrax peptide. However, in some embodiments, an epitope tag can be placed within the amino acid sequence of an anthrax peptide. In some embodiments, an epitope tag can be used a linker to join an anthrax peptide to another peptide or another type of molecule. In some embodiments a linker can be Ac-Cys-Gly-Gly-Gly (SEQ ID NO:3). The presence of such epitope-tagged forms of an anthrax peptide can be detected using an antibody against the epitope tag. Also, provision of the epitope tag enables the anthrax peptide to be readily purified by affinity purification using an anti-tag antibody or another type of affinity matrix that binds to the epitope tag; this also can be useful for binding the anthrax peptide to a support for heterogeneous screening methods. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto [Evan et al., Molecular and Cellular Biology, 5:3610-3616 (1985)]; and the Herpes Simplex virus glycoprotein D (gD) tag and its antibody [Paborsky et al., Protein Engineering, 3(6):547-553 (1990)]. Other tag polypeptides include the Flag-peptide [Hopp et al., BioTechnology, 6:1204-1210 (1988)]; the KT3 epitope peptide [Martin et al., Science, 255:192-194 (1992)]; tubulin epitope peptide [Skinner et al., J. Biol. Chem., 266:15163-15166 (1991)]; and the T7 gene 10 protein peptide tag [Lutz-Freyermuth et al., Proc. Natl. Acad. Sci. USA, 87:6393-6397 (1990)].

By "nucleic acid", "oligonucleotide", "polynucleotide", and grammatical equivalents herein are meant at least two nucleotides covalently linked together. A nucleic acid of the present invention will generally contain phosphodiester bonds, although in some cases, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments. Determining the type of nucleotides and their position within a nucleic acid depends at least in part on the intended use of the nucleic acid and is within the abilities of the skilled artisan.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

By "anthrax nucleic acid," and grammatical equivalents herein are meant a recombinant, isolated and/or synthetic nucleic acid comprising a sequence homologous or identical to all of part the anthrax bacterium genome, extrachromosomal element (e.g., pX01, pX02), and mRNA, particularly including fragments. In various exemplary embodiments, an "anthrax nucleic acid" can have an overall homology to the nucleotide sequences of anthrax that is greater than about 75%, greater than about 80%, greater than about 85% and greater than 90%. In some embodiments the homology can be as high as about 93 to 95 to 98% to 100%. Homology in this context means sequence similarity or identity, with identity being preferred. In some embodiments, an anthrax nucleic acid can encode an anthrax peptide. In various exemplary embodiments, an anthrax nucleic acid can be about 8-100 nucleotides in length, about 8-40 nucleotides in length, or about 8 to 20 nucleotides in length. In some embodiments, an anthrax nucleic acid can comprise from about 1%, 5%, 10%, 15%, 20%, 25%, 30%, 35%, 40%, 45%, 50%, 55%, 60%, 65%, 60%, 75%, 80%, 85%, 90%, 95%, to about 100% of the number of nucleic acids of full length anthrax nucleic acid or a full-length anthrax ORF.

In some embodiments, an anthrax nucleic acid can express an anthrax peptide. Therefore, in some embodiments an anthrax nucleic acid can include a promoter (e.g., inducible or constitutive), enhancer sequences (e.g., IE1 enhancer), introns sequences, transcriptional regulatory elements, polyadenylation sequences (e.g., BGH polyadenylation sequence) and the like suitable for expression of an anthrax peptide in eukaryotic or prokaryotic organism or in vitro expression. Vectors suitable for expression include but are not limited to plasmids (e.g., pUC18, VR1012), baculovirus vectors, retrovirus vectors, adenovirus vectors, adeno-associated virus vectors, herpesvirus vectors, vaccinia virus vectors, SV50, M13, yeast artificial chromosomes, and the like. In some embodiments, an anthrax nucleic can be used as a nucleic acid vaccine. Therefore, in some embodiments, an anthrax nucleic acid can be used to treat anthrax in a subject.

As is known in the art, a number of different programs can be used to identify whether a peptide or nucleic acid has sequence identity or similarity to a known sequence. Sequence identity and/or similarity can be determined using standard techniques known in the art, including, but not limited to, the local sequence identity algorithm of Smith and Waterman, Adv. Appl. Math. 2:482 (1981), by the sequence identity alignment algorithm of Needleman & Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387-395 (1984), preferably using the default settings, or by inspection. Preferably, percent identity can be calculated by FastDB based upon the following parameters: mismatch penalty of 1; gap penalty of 1; gap size penalty of 0.33; and joining penalty of 30, "Current Methods in Sequence Comparison and Analysis" in Macromolecule Sequencing and Synthesis, Selected Methods and Applications, pp 127-149, Alan R. Liss, Inc. (1988).

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle, J. Mol. Evol. 35:351-360 (1987); the method is similar to that described by Higgins and Sharp CABIOS 5:151-153 (1989). Useful PILEUP parameters including a default gap weight of 3.00, a default gap length weight of 0.10, and weighted end gaps.

Another example of a useful algorithm is the BLAST algorithm, described in Altschul et al., J. Mol. Biol. 215, 403-410, (1990) and Karlin et al., Proc. Natl. Acad. Sci. USA 90:5873-5787 (1993). A particularly useful BLAST program is the WU-BLAST-2 program which was obtained from Altschul et al., Methods in Enzymology, 266: 460-480 (1996); http://blast.wustl/edu/blast/README.html). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. Nucleic Acids Res. 25:3389-3402. Gapped BLAST uses BLOSUM-62 substitution scores; threshold T parameter set to 9; the two-hit method to trigger ungapped extensions; charges gap lengths of k a cost of 10+k; Xu set to 16, and Xg set to 40 for database search stage and to 67 for the output stage of the algorithms. Gapped alignments are triggered by a score corresponding to ~22 bits.

A percent amino acid and nucleic acid sequence identity value can be determined by the number of matching identical sequence positions divided by the total number of positions of the "longer" sequence in the aligned region. The "longer" sequence is the one having the most actual residues in the aligned region (gaps introduced by WU-Blast-2 to maximize the alignment score can be ignored).

In some embodiments, an alignment may include the introduction of gaps in the sequences to be aligned. In addition, the skilled artisan will appreciate that in some embodiments, the percentage of sequence identity can be determined based on the number of identical sequence positions in relation to the total number of sequence positions. Thus, for example, sequence identity can be determined using the number of positions in the shorter sequence.

In percent identity calculations relative weight is not assigned to various manifestations of sequence variation, such as, insertions, deletions, substitutions, etc. Therefore, in sequence identity determinations, only identities are scored positively (+1) and all forms of sequence variation including gaps are assigned a value of "0", which obviates the need for a weighted scale or parameters for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

By "antibody" and grammatical equivalents herein are meant polyclonal and monoclonal antibody (mAb). Methods of preparation and purification of monoclonal and polyclonal antibodies are known in the art (see e.g., Harlow and Lane, Antibodies: A Laboratory Manual (New York: Cold Spring Harbor Laboratory Press, 1988).

By "anthrax antibody" and grammatical equivalents herein refer to a polyclonal or monoclonal antibody that can be induced by a disclosed anthrax peptide according to the methods disclosed herein. In some embodiments, an anthrax antibody can bind to a disclosed anthrax peptide. In some embodiments, an anthrax antibody prevents anthrax disease and/or ameliorates a symptom of anthrax disease in a subject.

Thus, in some embodiments, an anthrax antibody can bind to anthrax (i.e., an etiologic agent of anthrax disease or an anthrax virulence factor). Without being bound by theory, in some embodiments, the binding of an anthrax antibody can substantially neutralize or inactivate an etiologic agent of anthrax disease or an anthrax virulence factor. Thus, in a preferred embodiment, anthrax antibodies are capable of reducing or eliminating a pathologic effect of anthrax. That is, the binding of anthrax antibodies to an etiologic agent of anthrax or an anthrax virulence factor may decrease or eliminate anthrax infectivity and/or virulence factor activity, including but not limited to, replication, virulence factor synthesis, virulence factor toxicity, resistance to immune effector mechanisms (e.g., phagocytosis), and the like. Generally, at least about a 25% decrease is preferred, with at least about 50% being particularly preferred and at least about a 95-100% decrease being especially preferred.

In various exemplary embodiments, anthrax antibodies can be generated in a subject by immunization with an anthrax peptide, such as, PA, LF, EF, PGA, BclA, including fragments as shown herein.

The terms "antibody" and "anthrax antibody," include antibody fragments and derivatives, as are known in the art, such as Fab, Fab', F(ab')2 or other antigen-binding subsequences of antibodies, such as, single chain antibodies (Fv for example), chimeric antibodies, etc., either produced by the modification of whole antibodies or those synthesized de novo using recombinant DNA technologies. The term antibodies further comprise polyclonal antibodies and mAbs which can be agonist or antagonist antibodies as well as antibodies that have been derivatized for example with PEG as known in the art or variants as described herein.

Anthrax antibodies of the invention can specifically bind to anthrax peptides. By "specifically bind" herein is meant that the anthrax antibodies have a binding constant in the range of at least about $10^{-4}$ to about $10^{-6}$ $M^{-1}$, with a preferred range being at least about $10^{-7}$ to at least about $10^{-9}$ $M^{-1}$. Thus, in preferred embodiments, anthrax antibodies can block the binding of a second antibody to anthrax and/or can block the binding of an anthrax peptide to a host cell. In some embodiments, anthrax antibodies can function as opsonins to facilitate phagocytosis of an anthrax bacterium. By "opsonin" and grammatical equivalents herein are meant any substance that binds to particulate antigens and facilitates their phagocytosis by Fc receptor bearing phagocytic cells. In a preferred embodiment, opsonizing antibodies can be IgM or IgG. These and other antibody isotypes and subtypes, depending on the subject, can activate the complement system resulting in the deposition of fragments of complement peptides (e.g., C3b, C3d, and C4b) which can further promote phagocytosis by binding to specific receptors (e.g., C3b receptors or C3d receptors) on phagocytic cells.

Once made, the anthrax compositions of the invention (e.g. anthrax antibodies and anthrax peptides) find use in a number of applications. Particularly preferred are therapeutic and prophylactic treatments as outlined below.

In a preferred embodiment, the anthrax compositions (e.g., anthrax peptides and anthrax antibodies) of the invention find use in the treatment of anthrax disease. "Treatment" refers to both therapeutic treatment and prophylactic treatment or preventative measures, wherein the object is to prevent or slow down (lessen) a targeted pathologic condition or disorder. By "host," "subject," "patient," "individual" and grammatical equivalents herein are meant those in need of treatment, such as, those with the disorder, as well as those prone to have the disorder, or those in whom the disorder is to be prevented. Thus, in various exemplary embodiments, a subject can be a human subject and wild or domestic herbivores, and the like, with human subjects being preferred.

In a preferred embodiment, anthrax antibody of the present invention can be administered to a subject in a therapeutically effective amount. Therefore, in some embodiments, anthrax antibody can be used to provide passive immunity to a subject. (Goodman and Gilman's The Pharmacological Basis of Therapeutics 1463-1486 (Hardman et al., ed., 10th ed., McGraw-Hill 2001 (ISBN 0-07-112432-2)) By "therapeutically effective amount", "pharmaceutically effective amount", and grammatical equivalents herein are meant an amount sufficient to produce the desired physiological effect or an amount capable of achieving the desired result, particularly for treatment of a disorder or disease condition, including reducing or eliminating one or more symptom of the disorder or disease or prevention or delaying the onset of at least one a disease symptom.

Therefore, a therapeutically effective amount of an anthrax antibody refers to an amount sufficient for treatment of anthrax. The amount may be different depending on whether prophylactic or therapeutic treatment is desired. Determining the dosages and times of administration for a therapeutically effective amount of antibody are well within the skill of the ordinary person in the art. Therefore, the skilled artisan will appreciate that these amounts may be adjusted depending on the severity of disease, susceptibility of the subject, age, weight, and type of subject, and the like.

In a preferred embodiment, anthrax peptides of the present invention find use as antibacterial compounds and vaccines. In various exemplary embodiments, anthrax peptides can be used alone or in various combinations of 2, 3, 4, or more peptides and formulations. In a preferred embodiment, the combinations of anthrax peptides can be substantially unique to the various life stages of anthrax bacterium (spore, vegetative bacterium). Therefore, the compositions disclosed herein can comprise an anthrax spore peptide and a peptide of a vegetative bacterium, an anthrax spore peptide and an anthrax exotoxin peptide, an anthrax exotoxin peptide and a peptide of a vegetative anthrax bacterium.

By "vaccine" herein is meant a treatment that increases the immunity of a subject to a particular disease. Therefore, as used herein "anthrax vaccine" refers to a treatment that increases the immunity of a subject to anthrax disease. Therefore, in some embodiments, a vaccine may be administered prophylactically, for example to a subject that is immunologically naïve (i.e., no prior exposure or experience with a disease). In some embodiments, a vaccine may be administered therapeutically to a subject who has been exposed to anthrax or has been previous infected with anthrax or is experiencing at least one disease symptom. Thus, a vaccine can be used to ameliorate a symptom associated with a disease. In a preferred embodiment, an anthrax vaccine is a therapeutically effective composition comprising one or more anthrax peptides including fragments thereof that induce an immune response to anthrax.

Various anthrax peptides can be formulated in various ways. In some embodiments, anthrax peptides can be formulated alone or in various combinations with other anthrax peptides. In some embodiments, anthrax peptides can be formulated as a mixture. In some embodiments, anthrax peptides can be modified in a way to form chimeric molecules comprising an anthrax peptide fused to one or more homologous or heterologous anthrax peptides or non-anthrax peptide. In various exemplary embodiments, a fusion can be a linear or branched fusion. In some embodiments, an anthrax peptide can be conjugated or cross-linked to one or more homologous or heterologous anthrax peptides or non-anthrax peptides, can be conjugated together, as described below. The administration of an anthrax peptide as a vaccine can be accomplished by various methods as known in the art. (Goodman and Gilman's The Pharmacological Basis of Therapeutics 1-30 (Hardman et al., ed., 10th ed., McGraw-Hill 2001 (ISBN 0-07-112432-2)). In a preferred embodiment, anthrax peptides contact one or more mucous membranes of a subject, including but not limited to, the nasopharynx, oropharynx, nares, buccal or oral cavity, vagina and colon. Generally, anthrax peptides can be formulated according to known methods to prepare pharmaceutically useful compositions, whereby therapeutically effective amounts of anthrax peptide are combined in admixture with a pharmaceutically acceptable carrier vehicle. Suitable vehicles and their formulation are well known in the art. Such compositions will contain pharmaceutically effective amount of anthrax peptide together with a suitable amount of vehicle in order to prepare pharmaceutically acceptable compositions for effective administration to a patient. The composition may include salts, buffers, carrier proteins such as serum albumin, targeting molecules to localize anthrax peptides at the appropriate site or tissue within the patient, and other molecules. The composition may include adjuvants as well. The formulation is chosen at the discretion of the practitioner and is dependent on the route of immunization, age and immune status of the patient, and severity of disease.

In a preferred embodiment, anthrax peptide vaccines comprise an adjuvant. "Adjuvant" as used herein refers to a nontoxic agent that can stimulate the immune system, thereby, enhancing, either quantitatively and/or qualitatively, the response to an anthrax peptide. By "mucosal adjuvant" and grammatical equivalents herein is meant an adjuvant suitable for administration at a mucosal membrane. In a preferred embodiment a mucosal adjuvant stimulates a mucosal immune response. In some embodiments, a mucosal adjuvant can be an isolated extract comprising a protein or lipid of a gram-negative bacterial cell well or outer layer, such as, an invasin protein or lipid A. In a preferred embodiment, a mucosal adjuvant can be an agonist of a toll-like receptor (e.g., TLR4). In a preferred embodiment, a mucosal adjuvant can be signaling transducer receptor of lipopolysaccharide (LPS). In a preferred embodiment, a mucosal adjuvant can stimulate innate immunity. In a preferred embodiment a mucosal adjuvant can be monophosphoryl lipid A (MPL). (U.S. Pat. Nos. 4,436,727, 4,436,728, 4,912,094; Baldridge et al. Expert Opin. Biol. Ther. 4:1129-1138; Persing et al. 2002. Trends Microbiol. 10:S32-37; Baldridge et al. 2000. Vaccine 18:2416-2425; Yang et al. 2002. Infect. Immun. 70:3557-3565; Baldrick et al. 2002. Regul. Toxicol. Pharmacol. 35:398-413). In a preferred embodiment, a mucosal adjuvant can be synthetic trehalose dicorynomycolate (TDM). In a preferred embodiment, a mucosal adjuvant can be a positively charged linear polysaccharide, for example, chitosan (e.g., chitosan glutamate), which is derived from the shells of crustaceans and is suitable for acting as a depot. (U.S. Pat. No. 6,391,318; U.S. Pat. No. 6,391,318 B1, U.S. Patent Application No. US2003039665, EP0865297, WO9720576; Bacon et al. 2000. Infect. Immun. 68:5764-5770; Illum. 2003. J. Control. Release. 87:187-198; Illum et al. 2001. Adv. Drug Deliv. Rev. 51:81-96; Davis. 1999. Pharm. Sci. Technol. Today 2:450-456; Jabbal-Gill et al. 1998. Vaccine 16:2039-2046; Lim et al. 2001. AAPS Pharm. Sci. Tech. 2:20; van der Lubben et al. 2001. Adv. Drug Deliv. Rev. 52:139-144; van der Lubben et al. 2001. Eur. J. Pharm. Sci. 14:201-207; McNeela et al. 2004. Vaccine 22:909-914; Mills et al. 2003. Infect. Immun. 71:726-732). In a preferred embodiment, a mucosal adjuvant can be a combination of two or more mucosal adjuvants. Invaplex and methods of use are described in U.S. Pat. Nos. 6,245,892, 6,277,379, 6,680374, and PCT Publication No. WO02/094190, all four of which are expressly incorporated by reference in their entirely. An Invaplex preferably finds use as a mucosal adjuvant to induce a mucosal immune response to anthrax peptides, such as, IgA. In another preferred embodiment, anthrax peptide vaccines comprise and an M cell targeting ligand. By "M cell targeting ligand" and grammatical equivalents herein are meant a compound that binds to an receptor on M cells. In this embodiment, the M cell targeting ligand preferably is selected from the group consisting of the protein al of a reovirus, or is (or is derived from) an adhesin of Salmonella or a poliovirus. In a most preferred embodiment, the M cell targeting ligand is a σ1 protein. M cell ligands target anthrax peptides to follicle associated epithelium or M cells by receptor-mediated endocytosis to induce mucosal immunity. M cell targeting ligands and methods of use are described in PCT Publication Nos. WO01/49867 and WO02/072015, both of which are expressly incorporated by reference.

Where sustained-release administration of an anthrax peptide is desired in a formulation with release characteristics suitable for the treatment of any disease or disorder requiring administration of the anthrax peptide, microencapsulation of the polypeptide is contemplated. Microencapsulation of recombinant proteins for sustained release has been successfully performed with human growth hormone (rhGH), interferon- (rhIFN-), interleukin-2, and MN rgp120. Johnson et al., Nat. Med., 2:795-799 (1996); Yasuda, Biomed. Ther., 27:1221-1223 (1993); Hora et al., Bio/Technology, 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010. The sustained-release formulations of polypeptides were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41.

Anthrax peptides can be administered in various formulations and in various amounts depending on factors including but not limited to the age, mass, immune status, route of immunization, and health of a subject. In some embodiments, an anthrax peptide can be administered to a human subject in a range from about 40 to about 200 μg peptide/dose. In various exemplary embodiments, the dose administered to a subject can be from about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, to about 250 μg peptide/dose, with higher and lower doses that can be contemplated. In some embodiments, a dose administered to a subject can be from about 1, 2, 3, 4, 5, 6, 7, 8, 9, to about 10, 15, 20, 30, 40, 50, 60, 70, 80, 90, to about 100 μg/kg body mass, with higher and lower doses than can be contemplate. The number of doses that can be administered as a function of time can be from about 1, 2, or about 3 doses over 1, 2, 3, or about 4 weeks but can be increased or decreased depending at least in part on the immune status of a subject.

"Pharmaceutically acceptable salt" refers to a salt of a compound of the invention which is made with counterions is understood in the art to be generally acceptable for pharmaceutical uses and which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucuronic or galacturonic acids and the like (see, e.g., Berge et al., J. Pharm. Sci. 66:1-19 (1977)).

"Pharmaceutically acceptable vehicle", "pharmaceutically acceptable carrier", and grammatical equivalents refer to a diluent, adjuvant, excipient, surfactant, preservative, stabilizer, chelating agent, or the like with which a compound of the invention (e.g., anthrax peptide or anthrax antibody) can be administered, as will be appreciated by those skilled in the art of pharmaceutical formulations. (U.S. Pat. No. 6,403,597) A wide variety of suitable pharmaceutical compositions are described, for example, in Remington's Pharmaceutical Sciences, 20th ed., 2001.

In a preferred embodiment, the compositions of the invention are anti-anthrax compounds. By "anti-anthrax" and grammatical equivalents herein are meant a compound that inhibits the replication of anthrax bacterium, inhibits anthrax exotoxin, or reduces an anthrax disease symptom. Thus, an anthrax peptide may be administered prophylactically, for example to a patient never previously exposed to anthrax bacterium, such that subsequent infection by anthrax is prevented. Alternatively, anthrax peptide may be administered therapeutically to a patient previously exposed or infected by anthrax. Anthrax peptides compounds may be administered per se, but are typically formulated and administered in the form of a pharmaceutical composition. The exact composition will depend upon, among other things, the method of administration, such as orally or parenterally, and will be apparent to those of skill in the art.

Formulations suitable for oral administration can consist of (a) liquid solutions, such as an effective amount of the active compound suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Suitable formulations for rectal or vaginal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, subcutaneous administration and intravenous administration are the preferred methods of administration.

A specific example of a suitable suspension formulation may include from about 0.5-30 mg/ml compound and one or more excipients selected from the group consisting of: about 200 mg/ml ethanol, about 1000 mg/ml vegetable oil (e.g., corn oil), about 600-1000 mg/ml fruit juice (e.g., grapefruit juice), about 400-800 mg/ml milk, about 0.1 mg/ml carboxymethylcellulose (or microcrystalline cellulose), about 0.5 mg/ml benzyl alcohol (or a combination of benzyl alcohol and benzalkonium chloride) and about 40-50 mM buffer, pH 7 (e.g., phosphate buffer, acetate buffer or citrate buffer or, alternatively 5% dextrose may be used in place of the buffer) in water.

A specific example of a suitable liposome suspension formulation may comprise from about 0.5-30 mg/ml compound, about 100-200 mg/ml lecithin (or other phospholipid or mixture of phospholipids) and optionally about 5 mg/ml cholesterol in water. For subcutaneous administration of certain PBI compounds, a liposome suspension formulation including 5 mg/ml compound in water with 100 mg/ml lecithin and 5 mg/ml compound in water with 100 mg/ml lecithin and 5 mg/ml cholesterol provides good results.

The formulations of compounds can be presented in unit-dose or multi-dose sealed containers, such as ampules and vials. Injection solutions and suspensions can be prepared from sterile powders, granules, and tablets of the kind previously described. In some embodiments, the disclosed compositions (e.g., anthrax peptides, vaccines, and anthrax antibodies) and formulations can be packaged in kits for administration to a subject, e.g., a container, preferably sealed, for storage prior to use and instructions for carrying out administration suitable for treatment of anthrax. For example, in some embodiments, a formulation can be suitable for administration to a mucosal surface and therefore can contain one or more unit doses of an anthrax vaccine. In some embodiments, a formulation can be suitable for parenteral administration and therefore can contain a one or more unit doses of an anthrax vaccine or anthrax antibody. In some embodiments, a kit can include a device suitable for administrating one or more of the disclosed compositions, including unit doses. Thus, in some embodiments, a kit can contain multiple formulations of various anthrax peptides and antibodies for administration via various devices, including but not limited to, droppers, swabs, aerosolizers, sufflators, nebulizers, inhalers, syringes, needles, dermal patches, and the like (e.g., Valois Monopowder Nasal Administration Device, Monopowder Administration Device).

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials, sufflators, or ampoules. Also, the unit dosage form can be a capsule, tablet, cachet, or lozenge itself, or it can be the appropriate number of any of these in packaged form. The composition can, if desired, also contain other compatible therapeutic agents, discussed in more detail, below.

In therapeutic use for the treatment of anthrax, the anthrax compositions (e.g., antibodies and peptides) utilized in the pharmaceutical methods to achieve therapeutic benefit. By "therapeutic benefit" is meant that the administration of compound leads to a beneficial effect in the patient over time. For example, therapeutic benefit can be achieved when the anthrax bacterium titer or load in the patient is either reduced or stops increasing or a symptom or an anthrax exotoxin is reduced or stops increasing. Therapeutic benefit is also achieved if the administration of compound slows or halts altogether the onset of adverse symptoms that typically accompany anthrax infections or exposure to an anthrax virulence factor (e.g., an anthrax exotoxin), regardless of the anthrax bacterium or anthrax exotoxin titer or load in the patient.

The anthrax peptides and/or anthrax antibodies may also be administered prophylactically in patients who are at risk of developing anthrax infection, or who have been exposed to anthrax bacterium, to prevent the development of anthrax infection or disease. For example, the anthrax peptides and/or compositions thereof may be administered to a patient likely to have been exposed to anthrax bacterium.

While the present teachings are described in connection with various embodiments, it is not intended that the present teachings be limited to such embodiments. Rather, the present teachings encompass various alternatives, modification, and equivalents, as will be appreciated by those skilled in the art.

Aspects of the present disclosure may be further understood in view of the following examples, which should not be construed as limiting the scope of the present disclosure in any way. All references cited herein are expressly incorporated by reference in their entirety for any purpose. If an expressly incorporated reference differs from or contradicts the present application, including but not limited to defined terms, term usage, described techniques, or the like, this application controls.

EXAMPLES

Example 1

Intranasal Vaccination with Protective Antigen

Protocol: Female Balb/c mice, 8 weeks old were immunized on days 0, 14, and day 28 with 10 µl total volume of vaccine per animal. Prior to immunization, mice were lightly anesthetized with isofluorane to effect (2-4%), and a 5 µl/nostril bolus was delivered to each nare. Retention of the vaccine within the nares was generally good, but when sneezing occurred it was noted.

Vaccine formulation: Mice were immunized with either 5 µg or 20 µg doses of PA. Lyophilized PA was obtained from List Biochemical (Cat. #171B, Lot #1712B) and reconstituted in water immediately prior to use, which brought the salt content to 5 mM HEPES/50 mM NaCl. MPL+TDM (MPL) (Sigma #M-6536, Lot #072K1313) was warmed to 40° C. and resuspended in 1 mL 150 mM NaCl immediately prior to use. Invaplex 50 (IPX50) (Lot #GNGO), obtained from Edwin V. Oaks (Walter Reed Army Institute of Research (WRAIR)), was stored at −80° C. and immediately prior to use was thawed on ice. Adjuvants were added to PA at 5 µl/dose just prior to use.

Adjuvants: IPX50 is an ion-exchange chromatography fraction of a water extract isolated from Shigella bacteria containing the Shigella invasion complex (U.S. Pat. Nos. 6,680,374, 6,277,379, 6,245,892. MPL is monophosphoryl lipid A and synthetic treholose dicorynomycolate in squalene and Tween 80.

Treatment Groups: See Table 1

TABLE 1

Treatment Groups

| Group # | Treatment | Short name | No. mice |
|---|---|---|---|
| 1 | MPL | MPL | 3 |
| 2 | Invaplex 50 | IPX | 3 |
| 3 | 5 µg PA/Invaplex 50 | PA5/IPX | 5 |
| 4 | 20 µg PA/Invaplex 50 | PA20/IPX | 5 |
| 5 | 5 µg PA/MPL + TDM | PA5/MPL | 5 |
| 6 | 20 µg PA/MPL + TDM | PA20/MPL | 5 |
| 7 | Naïve | Naïve | 3 |

Sampling: Fecal and blood samples were collected from mice prior to the initial vaccination (day 0) and on days 27 and 56 (prior to boosts).

Anthrax Lethal Toxin Challenge: One week following collection of final samples, mice were subjected to an intravenous challenge with approximately 6 $LD_{50}$ of *B. anthracis* Lethal Toxin (LeTx). PA (60 µg) and LF (30 µg) (List Biochemical; PA #171B, Lot #1712B; LF #172B, Lot #1721B) were injected via tail vein in a total volume of 100 µl PBS. Mice were observed every 15 minutes for 16 hours post-injection, and hourly for hours 20 through 36. Thereafter, mice were checked every 6-8 hours until Day 7 (168 hours). Time to death (TTD) was recorded for each mouse that died. Mice living at 168 hours were survivors (S).

Serum IgG responses: Serum anti-PA IgG was measured by ELISA (Table 2. Six rows of wells in a 96 well plate (Rows C-G) were coated with 1 µg/ml PA in phosphate buffered saline (PBS) pH7.2. Rows A and B were coated with serial dilutions (1:2) of mouse IgG (Sigma 1-5381), beginning at 1 µg/ml in PBS, and continuing to ~2 ng/ml in column 10, to serve as standards. Absorbances from these wells were used to plot a standard curve using SoftMax Pro software. Wells A11, A12, B11 and B12 were blanks. The serum samples were diluted from 1:100 to 1:3200 (unless otherwise noted) in PBS with 0.05% Tween 20 and 3% fetal bovine serum (FBS). Detection was via HRP-conjugated antibody (Southern Biotech) and ABTS (Pierce Cat #37615). Each sample replicate was run on separate plates, with at least 2 analyses performed per sample. Sample absorbances were used to interpolate antibody concentration from the standard curves. Data was then exported to Excel (Microsoft®) for further analysis. If the CV (coefficient of variation, or 100*Standard Deviation/Mean) for the replicates was greater than 25, another replicate was performed. The exception to this rule was where the mean results were less than 10 μg/ml, in which case a CV of 150 was tolerated. Sample results reading above the standard curve range were deemed out of range, and were reanalyzed using a starting dilution of 1:1000.

Serum IgG: Serum drawn prior to the initial vaccination showed no measurable recognition of PA (data not shown). Serum anti-PA IgG responses were also measured at 4 and 8 weeks (FIG. 1). The 4 week samples reflected responses of animals 2 weeks following the first boost. At that time point, one mouse (out of five) immunized with PA5/IPX50 mounted a measurable IgG response of 10 μg/ml, however, none of the mice receiving PA5/MPL responded positively. Four of five mice receiving PA20/IPX50 also had measurable antigen-specific IgG levels (5-40 μg/ml, mean of 13 μg/ml for all five mice). Three of five mice receiving PA20/MPL responded (9-15 μg/ml, mean of 7 μg/ml for the group of five mice). The two vaccines containing 20 μg PA were not statistically different (p<0.44).

TABLE 2

ELISA

| | 1 | 2 | 3 | 4 | 5 | 6 | 7 |
|---|---|---|---|---|---|---|---|
| A | IgG 1:100 | IgG 1:200 | IgG 1:400 | IgG 1:800 | IgG 1:1600 | IgG 1:3200 | IgG 1:6400 |
| B | IgG 1:100 | IgG 1:200 | IgG 1:400 | IgG 1:800 | IgG 1:1600 | IgG 1:3200 | IgG 1:6400 |
| C | Mouse1 1:100 | Mouse2 1:100 | Mouse3 1:100 | Mouse4 1:100 | Mouse5 1:100 | Mouse6 1:100 | Mouse7 1:100 |
| D | Mouse1 1:200 | Mouse2 1:200 | Mouse3 1:200 | Mouse4 1:200 | Mouse5 1:200 | Mouse6 1:200 | Mouse7 1:200 |
| E | Mouse1 1:400 | Mouse2 1:400 | Mouse3 1:400 | Mouse4 1:400 | Mouse5 1:400 | Mouse6 1:400 | Mouse7 1:400 |
| F | Mouse1 1:800 | Mouse2 1:800 | Mouse3 1:800 | Mouse4 1:800 | Mouse5 1:800 | Mouse6 1:800 | Mouse7 1:800 |
| G | Mouse1 1:1600 | Mouse2 1:1600 | Mouse3 1:1600 | Mouse4 1:1600 | Mouse5 1:1600 | Mouse6 1:1600 | Mouse7 1:1600 |
| H | Mouse1 1:3200 | Mouse2 1:3200 | Mouse3 1:3200 | Mouse4 1:3200 | Mouse5 1:3200 | Mouse6 1:3200 | Mouse7 1:3200 |

| | 8 | 9 | 10 | 11 | 12 |
|---|---|---|---|---|---|
| A | IgG 1:12,800 | IgG 1:25,600 | IgG 1:51,200 | Blank | Blank |
| B | IgG 1:12,800 | IgG 1:25,600 | IgG 1:51,200 | Blank | Blank |
| C | Mouse8 1:100 | Mouse9 1:100 | Mouse10 1:100 | Mouse11 1:100 | Mouse12 1:100 |
| D | Mouse8 1:200 | Mouse9 1:200 | Mouse10 1:200 | Mouse11 1:200 | Mouse12 1:200 |
| E | Mouse8 1:400 | Mouse9 1:400 | Mouse10 1:400 | Mouse11 1:400 | Mouse12 1:400 |
| F | Mouse8 1:800 | Mouse9 1:800 | Mouse10 1:800 | Mouse11 1:800 | Mouse12 1:800 |
| G | Mouse8 1:1600 | Mouse9 1:1600 | Mouse10 1:1600 | Mouse11 1:1600 | Mouse12 1:1600 |
| H | Mouse8 1:3200 | Mouse9 1:3200 | Mouse10 1:3200 | Mouse11 1:3200 | Mouse12 1:3200 |

Serum ELISA: Serum anti-PA IgG was measured by ELISA. As shown in Table 2, two rows of a 96-well plate were coated with two-fold serial dilutions of mouse IgG (Sigma 1-5381), beginning at 1 μg/ml in PBS, and continuing to 2 ng/ml in column 10, to serve as standards. Each row served as a replicate. The remaining four wells in the two rows served as blanks. Remaining wells of the plate were coated with 1 μg/ml PA in PBS pH7.2. Coating continued overnight at 4° C. under high humidity. Wells were washed three times with PBS/0.05% Tween 20 (PBST), blocked 1 hour at room temperature with PBST+3% FBS. Serum samples were serially diluted two-fold in PBST/FBS from 1:100 to 1:3,200. Serum dilutions were incubated on plates at 4° C. overnight in high humidity. After again washing wells three times with PBST, mouse antibodies binding to PA were detected via 1:1000 dilution of HRP-conjugate goat anti-mouse IgG (Southern Biotech, #1030.05, Lot #D240-N742G) diluted into PBST/FBS, and incubated on wells for 1.5 hour at room temperature. Wells were washed three times with PBST, and the plate developed with ABTS (Pierce Cat #37615) for 30 minutes at room temperature. $OD_{405}$ readings were taken and values from the standards were plotted into a standard curve using SoftMax Pro software. Sample absorbencies were used to interpolate antibody concentration from the standard curves. Data was exported to Excel (Microsoft®) for further analysis. If the CV (coefficient of variation, or 100*Standard Deviation/Mean) for the replicates was greater than 25, another replicate was performed. The exception to this rule was where the mean results were less than 10 μg/ml, in which case a CV of 150 was tolerated. Sample results reading above the standard curve range were deemed out of range, and were reanalyzed using a starting dilution of 1:1000. Sera from 12 mice were run on each plate (one per column), and each sample was replicated on a separate plate. At least 2 analyses were performed on each sample.

At 8 weeks, the mice immunized with PA20/IPX responded quite variably (29, 92, 96, 216 and 321 μg/ml), but all had positive values (treatment mean 150 μg/ml). Similar results were seen with the PA20/MPL immunized mice, in that responses were variable (19, 82, 104, 162 and 221 μg/ml), and the treatment mean (118 μg/ml), although numerically lower, was statistically similar to that of PA20/IPX (p<0.61). All mice immunized with PA5/IPX had positive responses at 8 weeks (15, 18, 18, 30 and 174 μg/ml, mean for treatment group (51 μg/ml), while none of the mice immunized with PA5/MPL had measurable anti-PA IgG levels. However, variability in responses to the PA5/IPX immunization was too great to show a significant difference from the PA5/MPL group (p<0.17).

Figure 2:
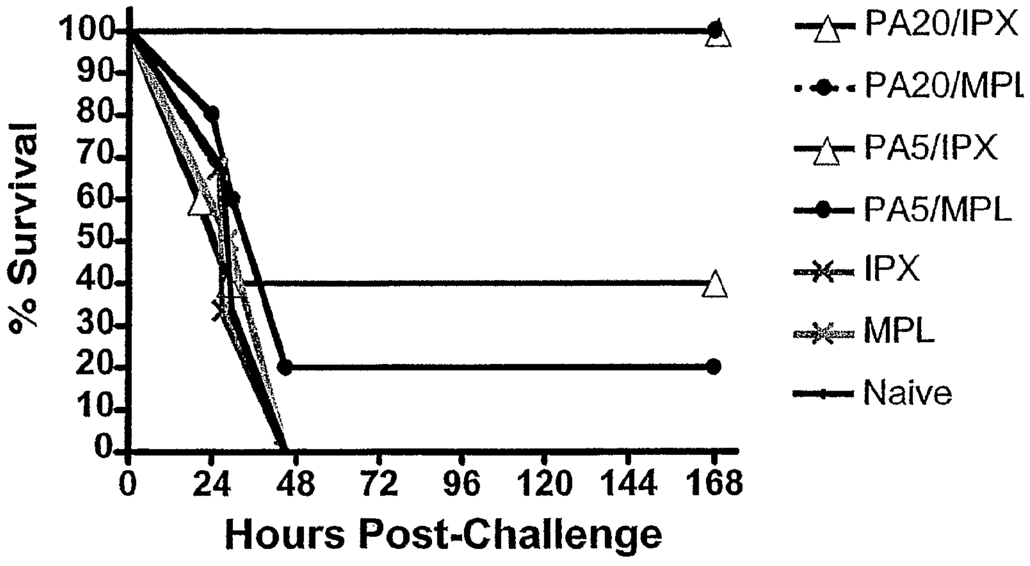
FIG. 2 shows survival of a lethal intravenous LeTx challenge by immunized mice (Example 1). The change in survivorship over time is indicated in hours post-challenge.

LeTx challenge: All mice were rested for one week after the final sampling at eight weeks. One week later on Feb. 5, 2003, each mouse received approximately 6 $LD_{50}$ of LeTx. TTD is shown in Table 3 and presented graphically in FIG. 2, with the exception that one mouse immunized with MPL only was excluded, as the LeTx entered subcutaneously rather than intravenously. Mice were either completely protected, or not at all, as TTD was not significantly extended in non-surviving mice with positive levels of anti-PA IgG over the TTDs of control mice. All mice receiving immunizations containing 20 μg PA survived, whether the immunization was adjuvanted by IPX or MPL.

TABLE 3

| LeTx Challenge | | | | |
|---|---|---|---|---|
| Group | Vaccine | TTD, hours | Median TTD, hours | Percent Surviving |
| 1 | MPL | 33, S*, 29 | 37 | 33 |
| 2 | IPX | 45, 26, 27 | 27 | 0 |
| 3 | PA5/IPX | 20, 20, 33, S, S | 29 | 40 |
| 4 | PA20/IPX | S, S, S, S, S | undefined | 100 |
| 5 | PA5/MPL | 24, 45, S, 45, 30 | 45 | 20 |
| 6 | PA20/MPL | S, S, S, S, S | undefined | 100 |
| 7 | Naïve | 27, 44, 30 | 30 | 0 |

TTD = Time To Death

*Received challenge dose subcutaneously rather than intravenously. S = Survived >168 h (7 days)

Mouse survival did not strictly correlate with level of serum IgG recognizing PA, as a mouse immunized with PA20/MPL survived with 18 µg/ml IgG, while two mice immunized with PA5/IPX50 with the same level of IgG did not survive. It is well known in the literature that protection from anthrax does not always correlate with titer. Although no LeTx administration difficulties were noted with the low-level responding PA20/MPL, it cannot be excluded that some of the toxin did not make it into the circulatory system.

This study tested IPX50 and MPL as mucosal adjuvants for intranasal (IN) immunization with PA. Intranasal immunization of mice with 20 µg PA adjuvanted either with IPX50 or MPL protected mice from an intravenous LeTx challenge.

Example 2

Intranasal Vaccination with Protective Antigen

Protocol: Female Balb/c mice, 17 weeks old, were immunized on days 0, 13, and 27 with 10 µl total volume of vaccine per animal. Prior to immunization, mice were lightly anesthetized with isofluorane to effect (2-4%), and 5 µl/nostril bolus was delivered to each nares. Retention of vaccine within the nares was generally good but when sneezing occurred it was noted.

Vaccine Formulation: Mice were immunized with either 5 µg, 10 µg, or 20 µg PA. Lyophilized PA was obtained from List Biochemical (Cat. #171B, Lot #1714BA) and reconstituted in water immediately prior to use, which brought the salt content to 5 mM HEPES/50 mM NaCl. Invaplex 50 was stored at −80° C. until immediately prior to use, at which time it was thawed on ice. MPL+TDM (MPL) (Sigma #M-6536, Lot #072K1313) was warmed to 40° C. and resuspended in 1 mL 150 mM NaCl immediately prior to use. Invaplex 50 (Lot #GNGO) was obtained from Edwin V. Oaks (Walter Reed Army Institute of Research (WRAIR)) Invaplex 50 was stored at −80° C. Immediately prior to use, Invaplex 50 was thawed on ice. Adjuvants were added to PA at 5 µl/dose immediately prior to use.

Adjuvants: Invaplex 50 is an ion-exchange chromatography fraction of a water extract isolated from Shigella bacteria containing the Shigella invasion complex (U.S. Pat. Nos. 6,680,374, 6,277,379, 6,245,892. MPL+TDM is monophosphoryl lipid A and synthetic treholose dicorynomycolate in squalene and Tween 80.

Treatment Groups: See Table 4.

TABLE 4

| Treatment Groups | | | |
|---|---|---|---|
| Group # | Treatment | Short name | No. mice |
| 1 | MPL + TDM | MPL | 3 |
| 2 | Invaplex 50 | IPX | 3 |
| 3 | 5 µg PA/Invaplex 50 | PA5/IPX | 5 |
| 4 | 10 µg PA/Invaplex 50 | PA10/IPX | 5 |
| 5 | 20 µg PA/Invaplex 50 | PA20/IPX | 5 |
| 6 | 5 µg PA/MPL + TDM | PA5/MPL | 5 |
| 7 | 10 µg PA/MPL + TDM | PA10/MPL | 5 |
| 8 | 20 µg PA/MPL + TDM | PA20/MPL | 5 |
| 9 | Naïve | Naïve | 3 |

Sampling: Fecal and blood samples were collected from the mice prior to the initial vaccination (day 0) and on days 27 and 56 (prior to boosts).

Anthrax Lethal Toxin Challenge: One week following collection of final samples, mice received an intravenous challenge with approximately 6 $LD_{50}$ of *B. anthracis* Lethal Toxin (LeTx). PA (60 µg) and LF (30 µg) (List Biochemical; PA #171B Lot #1712B; LF #172B Lot #1721B) were injected via tail vein in a total volume of 100 µl PBS. Mice were observed every 15 minutes for 16 hours post-injection, and hourly for hours 20 through 36. Thereafter, mice were checked every 6-8 hours for 7 days (168 hours). Time to death was recorded for each mouse that died. Mice that were still alive at 168 hours were defined as survivors.

Serum ELISA: Serum anti-PA IgG was measured by ELISA. Plate layout is shown in Table 5. The Softmax Pro template was originally designed by Susan Wimer-Mackin and updated by Sarah J. Warwood. Two rows of a 96-well plate were coated with two-fold serial dilutions of mouse IgG (Sigma 1-5381), beginning at 1 µg/ml in PBS, and continuing to 2 ng/ml in column 10, to serve as standards. Each row served as a replicate. The remaining four wells in the two rows served as blanks. Remaining wells of the plate were coated with 1 µg/ml PA in phosphate buffered saline (PBS) pH7.2). Coating continued overnight at 4° C. under high humidity. Wells were washed three times with PBS/0.05% Tween 20 (PBST), blocked for 1 hour at room temperature with PBST+3% fetal bovine sera (FBS). Serum samples were serially diluted two-fold in PBST/FBS beginning at 1:100 to 1:3,200. Serum dilutions were incubated on plates at 4° C. overnight in high humidity. After washing wells three times with PBST, mouse antibodies binding to PA were detected via 1:1000 dilution of HRP-conjugate goat anti-mouse IgG (Southern Biotech, #1030.05, Lot #D240-N742G) diluted into PBST/FBS, and incubated on wells for 1.5 hours at room temperature. Wells were again washed three times with PBST, and the plate developed with ABTS (Pierce Cat #37615) for 30 minutes at room temperature. $OD_{405}$ readings were taken and values from the standards plotted into a standard curve using SoftMax Pro software. Sample absorbencies were used to interpolate antibody concentration from the standard curves. Data was exported to Excel (Microsoft®) for further analysis. If the CV (coefficient of variation, or 100*Standard Deviation/Mean) for the replicates was greater than 25, another replicate was performed. The exception to this rule was where the mean results were less than 10 µg/ml, in which case a CV of 150 was tolerated. Sample results reading above the standard curve range were deemed out of range, and were reanalyzed using a starting dilution of 1:1000. Sera from 12 mice were run on each plate (one per column), and each sample was replicated on a separate plate. At least 2 analyses were performed on each sample.

TABLE 5

| ELISA | | | | | | | |
|---|---|---|---|---|---|---|---|
| | 1 | 2 | 3 | 4 | 5 | 6 | 7 |
| A | IgG 1:100 | IgG 1:200 | IgG 1:400 | IgG 1:800 | IgG 1:1600 | IgG 1:3200 | IgG 1:6400 |
| B | IgG 1:100 | IgG 1:200 | IgG 1:400 | IgG 1:800 | IgG 1:1600 | IgG 1:3200 | IgG 1:6400 |
| C | Mouse1 1:100 | Mouse2 1:100 | Mouse3 1:100 | Mouse4 1:100 | Mouse5 1:100 | Mouse6 1:100 | Mouse7 1:100 |
| D | Mouse1 1:200 | Mouse2 1:200 | Mouse3 1:200 | Mouse4 1:200 | Mouse5 1:200 | Mouse6 1:200 | Mouse7 1:200 |
| E | Mouse1 1:400 | Mouse2 1:400 | Mouse3 1:400 | Mouse4 1:400 | Mouse5 1:400 | Mouse6 1:400 | Mouse7 1:400 |
| F | Mouse1 1:800 | Mouse2 1:800 | Mouse3 1:800 | Mouse4 1:800 | Mouse5 1:800 | Mouse6 1:800 | Mouse7 1:800 |
| G | Mouse1 1:1600 | Mouse2 1:1600 | Mouse3 1:1600 | Mouse4 1:1600 | Mouse5 1:1600 | Mouse6 1:1600 | Mouse7 1:1600 |
| H | Mouse1 1:3200 | Mouse2 1:3200 | Mouse3 1:3200 | Mouse4 1:3200 | Mouse5 1:3200 | Mouse6 1:3200 | Mouse7 1:3200 |
| | | | 8 | 9 | 10 | 11 | 12 |
| | | A | IgG 1:12,800 | IgG 1:25,600 | IgG 1:51,200 | Blank | Blank |
| | | B | IgG 1:12,800 | IgG 1:25,600 | IgG 1:51,200 | Blank | Blank |
| | | C | Mouse8 1:100 | Mouse9 1:100 | Mouse10 1:100 | Mouse11 1:100 | Mouse12 1:100 |
| | | D | Mouse8 1:200 | Mouse9 1:200 | Mouse10 1:200 | Mouse11 1:200 | Mouse12 1:200 |
| | | E | Mouse8 1:400 | Mouse9 1:400 | Mouse10 1:400 | Mouse11 1:400 | Mouse12 1:400 |
| | | F | Mouse8 1:800 | Mouse9 1:800 | Mouse10 1:800 | Mouse11 1:800 | Mouse12 1:800 |
| | | G | Mouse8 1:1600 | Mouse9 1:1600 | Mouse10 1:1600 | Mouse11 1:1600 | Mouse12 1:1600 |
| | | H | Mouse8 1:3200 | Mouse9 1:3200 | Mouse10 1:3200 | Mouse11 1:3200 | Mouse12 1:3200 |

Figure 3:
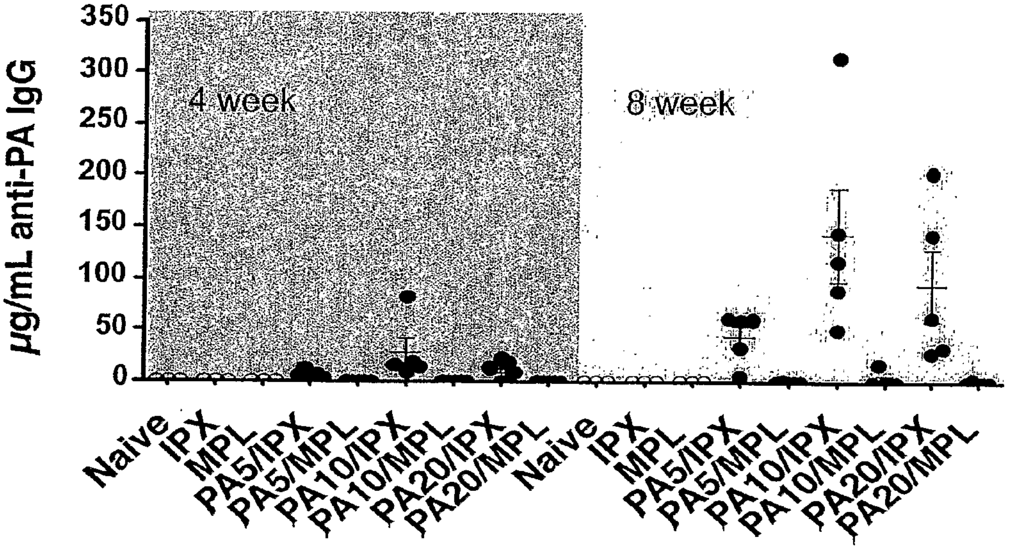
FIG. 3 shows ELISA results for sera collected at 4 weeks (Left) and 8 weeks (Right) following the initial vaccination (Example 2). The value of each individual mouse is indicated by a circle. Mean values for each treatment ±standard error of the mean are indicated by bars. The PA content of immunizations is indicated in the horizontal axis labels.

Serum IgG: Serum drawn prior to the initial vaccination showed no measurable recognition of PA (data not shown). Serum anti-PA IgG responses were also measured at 4 and 8 weeks (FIG. 3). The 4 week samples reflected responses of animals 2 weeks following the first boost. At that time point, four out of five mice immunized with PA5/IPX mounted measurable IgG responses (range of 3-12 μg/ml, mean for entire group 5 μg/ml). All five mice immunized with PA10/IPX had measurable responses, with one mouse recording a very significant 82 μg/ml (range of 9-82 μg/ml, mean of 28 μg/ml). Four of five mice receiving PA20/IPX also had measurable antigen-specific IgG levels (range of 9-22 μg/ml, mean of 12 μg/ml for all five mice).

Mice immunized with PA20/IPX responded at 8 weeks (27, 204, 32, 62 and 143 μg/ml; treatment mean 93 μg/ml). Results with PA10/IPX immunized mice (145, 315, 117, 89 and 50 μg/ml) (treatment mean 143 μg/ml) were statistically similar to PA20/IPX immunized mice ($p<0.41$). All mice immunized with PA5/IPX had positive responses at 8 weeks (61, 60, 33, 59 and 4 μg/ml, mean for treatment group (43 μg/ml). Two mice immunized with PA+MPL mounted measurable anti-PA IgG responses. One of those mice was immunized with PA10/MPL had 17 μg/ml anti-PA IgG, and the other was immunized with PA20/MPL had 3 μg/ml.

Figure 4:
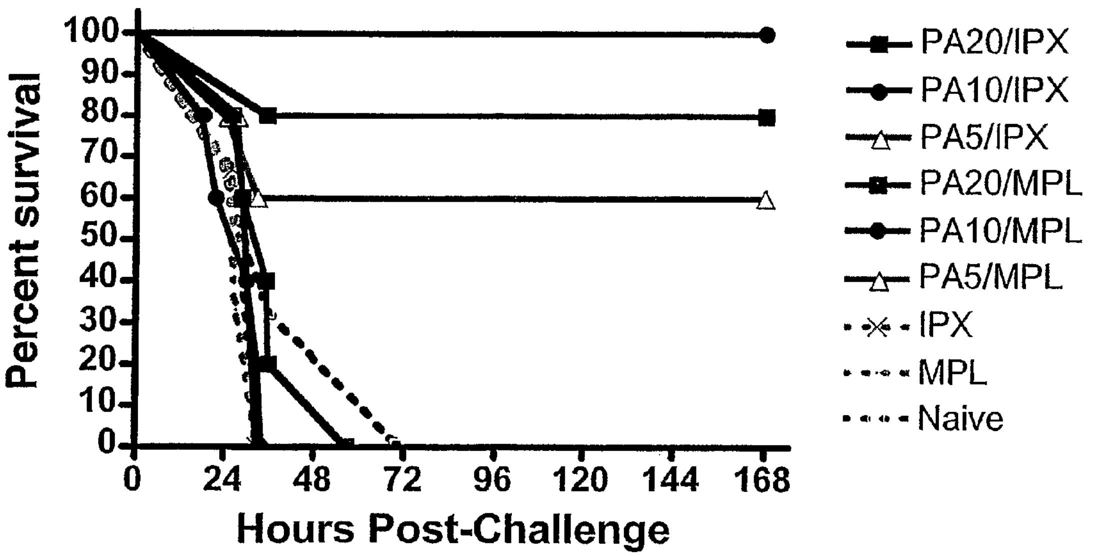
FIG. 4 shows survival of a lethal intravenous LeTx challenge by immunized mice (Example 2). The change in survivorship over time is indicated in hours post-challenge. For PA-containing immunization groups, n=5. For naive and IPX groups, n=3.

LeTx challenge: All mice were rested for one week after the final sampling at eight weeks. Each mouse received approximately 6 $LD_{50}$ LeTx. Time to death (TTD) is shown in Table 6 and presented graphically in FIG. 4. Mice were either completely protected, or not at all, as TTD was not significantly extended in non-surviving mice with positive levels of anti-PA IgG over the TTDs of control mice. All mice receiving PA10/IPX50, four out of the five mice receiving PA20/IPX50 and three of five mice receiving PA5/IPX50 survived the challenge. The PA20/IPX50 mouse that died had relatively low anti-PA IgG (32 μg/ml), as did one of the PA5/IPX50 mice that died (4 μg/ml). The other PA5/IPX50 mouse that died had 60 μg/ml anti-PA IgG idea that anti-PA titers do not necessarily correlate with toxin neutralization titers. Only one animal receiving PA adjuvanted with MPL survived, and we questioned at the time of challenge if all of that mouse's LeTx was given intravenously. This mouse had a barely measurable anti-PA IgG response in its serum (<1 μg/ml), suggesting that the challenge was indeed incompletely given.

TABLE 6

| LeTx Challenge | | | | |
|---|---|---|---|---|
| Group | Treatment | TTD* (hr) | Median TTD (hr) | Number Surviving |
| 1 | MPL | 27, 33, 25 | 27 | 0/3 |
| 2 | IPX50 | 33, 33, 26 | 33 | 0/3 |
| 3 | PA5/IPX50 | S, 33, S, S, 24 | undefined | 3/5 |
| 4 | PA10/IPX50 | S, S, S, S, S, | undefined | 5/5 |
| 5 | PA20/IPX50 | S, S, 35, S, S, | undefined | 4/5 |
| 6 | PA5/MPL | 29, 33, 27, 33, S* | 33 | 1/5 |
| 7 | PA10/MPL | 30, 18, 33, 34, 22 | 30 | 0/5 |
| 8 | PA20/MPL | 35, 29, 57, 36, 26 | 35 | 0/5 |
| 9 | Naïve | 35, 24, 71 | 35 | 0/3 |

TTD = Time to death

*Received at last past of challenge dose subcutaneously rather than intravenously S = Survived >168 hrs (7 days) after 6 $LD_{50}$ LeTx i.v.

Mouse survival did not strictly correlate with level of serum IgG recognizing PA. It is well known in the literature that protection from anthrax does not always correlate with titer.

Mean serum anti-PA IgG responses for Example 1 and Example 2 are shown in Table 7. No statistical differences between the two studies were detected for the PA/IPX50 treatments.

TABLE 7

| Mean anti-PA IgG Examples 1 & 2 | | | | |
|---|---|---|---|---|
| | 4 weeks | | 8 weeks | |
| Study | Ex. 1 | Ex. 2 | Ex. 1 | Ex. 2 |
| MPL | 0 | 0 | 0 | 0 |
| IPX | 0.0 | 0.0 | 0.0 | 0.0 |
| PA5/IPX50 | 2.0 | 5.2 | 51.0 | 43.2 |
| PA10/IPX50 | — | 27.7 | — | 143.3 |
| PA20/IPX50 | 13.4 | 12.2 | 150.7 | 93.6 |

TABLE 7-continued

| Mean anti-PA IgG Examples 1 & 2 | | | | |
|---|---|---|---|---|
| | 4 weeks | | 8 weeks | |
| Study | Ex. 1 | Ex. 2 | Ex. 1 | Ex. 2 |
| PA5/MPL | 0.0 | 0.0 | 0.0 | 0.1 |
| PA10/MPL | — | 0.0 | — | 3.4 |
| PA20/MPL | 7.2 | 0.0 | 117.5 | 0.6 |
| Naïve | 0.0 | 0.0 | 0.0 | 0.0 |

Example 3

Intranasal and Intraperitoneal Vaccination with Protective Antigen

Protocol: Female C57B1 mice, 16 weeks old, were immunize on Days 0 and 21 with 23 μg PA. Intraperitoneal (IP) immunizations were in a total volume of 100 μl containing 5 μl MPL per the manufacturer's directions. IN immunizations were in a total volume of 10 μl, and each contained 5 μg IPX50. For IN immunizations, a 5 μl/nostril bolus was delivered to each nares after lightly anesthetizing the mouse via isofluorine to effect.

Nanoparticles: Nanoparticles (NPs) were 20% nickel chelate, 32% EAPDA, 48% PCDA Na. PA in the form of a histidine tagged (His-tagged) recombinant protein was purified via IMAC (Batch 4, May 17, 2002). His-tagged PA was used in vaccines where the PA was bound to NPs (designated PA*NP) and in PA vaccines that did not contain NPs. All other PA containing vaccines utilized native, non-His-tagged PA.

Vaccine formulation: His-tagged PA was bound to NPs with gentle mixing at 4° C. overnight immediately prior to immunization. Non-conjugated NPs were treated similarly, only PA was not His-tagged, and thus was not suitable to bind NPs. Adjuvants were added to vaccines at 5 μl/dose immediately prior to use. PA-containing vaccines had 23 μg/dose. Parenteral vaccines were diluted up to 100 μl each with 150 mM NaCl. MPL (Sigma #M-6536, Lot #42K1185) was warmed to 40° C. and resuspended in 1 mL 150 mM NaCl just prior to use. IPX50 (lot #GNGO) was obtained from Edwin V. Oaks (WRAIR).

IPX50 was stored at −80° C. until immediately prior to use and thawed on ice. Adjuvants were added to PA at 5 μl/dose immediately prior to use.

Adjuvants: IPX50 is an ion-exchange chromatography fraction of a water extract isolated from Shigella bacteria containing the Shigella invasion complex. MPL is composed of monophosphoryl lipid A and synthetic treholose dicorynomycolate in squalene and Tween 80.

Treatment groups: Treatment groups are shown in Table 8. Negative controls were Naïve mice, and mice receiving either nanoparticles and MPL (IP), nanoparticles and Invaplex (IN) or Invaplex (IN) alone without the addition of PA. PA/MPL was included as a positive control.

TABLE 8

| Treatment Groups | | | | |
|---|---|---|---|---|
| Group # Treatment | | Short name | Route | No. mice |
| 1 | NP/MPL | NP/MPL | IP | 3 |
| 2 | NP/Invaplex 50 | NP/IPX | IN | 3 |
| 3 | PA/MPL | PA/MPL | IP | 5 |
| 4 | PA/Invaplex 50 | PA/IPX | IN | 5 |
| 5 | PA bound NP/MPL | PA * NP/MPL | IP | 5 |
| 6 | PA bound NP/Invaplex 50 | PA * NP/IPX | IN | 5 |
| 7 | Naïve | Naïve | — | 3 |
| 8 | PA unbound NP/MPL | PA/NP/MPL | IP | 5 |
| 9 | PA unbound NP/ Invaplex 50 | PA/NP/IPX | IN | 5 |
| 10 | Invaplex only | IPX | IN | 3 |

Sampling: Fecal and blood samples were collected from the mice prior to the initial vaccination (Day 0) and on Days 21 and 56. Mice were boosted with a repeat of the initial vaccination after the Day 21 samples were collected. Animals were sacrificed at the end of this study and the serum was collected and stored.

Serum ELISA: Serum anti-PA IgG was measured by ELISA (Table 9). Two rows of a 96-well plate were coated with two-fold serial dilutions of mouse IgG (Sigma I-5381) from 1 μg/ml in PBS to 2 ng/ml in column 10 to serve as standards. Each row served as a replicate. The remaining four wells in the two rows served as blanks. Remaining wells of the plate were coated with 1 μg/ml PA in PBS pH7.2. Coating continued overnight at 4° C. under high humidity. Wells were washed three times with PBS/0.05% Tween 20 (PBST), blocked 1 hour at room temperature with PBST+3% FBS. Serum samples were serially diluted two-fold in PBST/FBS from 1:100 to 1:3,200. Serum dilutions were incubated on plates at 4° C. overnight in high humidity. After again washing wells three times with PBST, mouse antibodies binding to PA were detected via 1:1000 dilution of HRP-conjugate goat anti-mouse IgG (Southern Biotech #1030.05, Lot #D240-N742G) diluted into PBST/FBS, and incubated on wells for 1.5 hours at room temperature. Wells were washed three times with PBST and the plate developed with ABTS (Pierce Cat #37615) for 30 minutes at room temperature. $OD_{405}$ readings were taken and values from the standards plotted into a standard curve using SoftMax Pro software. Sample absorbencies were used to interpolate antibody concentration from the standard curves. Data was exported to Excel for further analysis. Sera from 12 mice were run on each plate (one per column), and each sample was replicated on a separate plate. At least 2 analyses were performed on each sample.

TABLE 9

| ELISA | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | IgG 1:100 | IgG 1:200 | IgG 1:400 | IgG 1:800 | IgG 1:1600 | IgG 1:3200 | IgG 1:6400 | IgG 1: 12:800 | IgG 1: 25:600 | IgG 1: 51:200 | Blank | Blank |
| B | IgG 1:100 | IgG 1:200 | IgG 1:400 | IgG 1:800 | IgG 1:1600 | IgG 1:3200 | IgG 1:6400 | IgG 1: 12:800 | IgG 1: 25:600 | IgG 1: 51:200 | Blank | Blank |

TABLE 9-continued

| | ELISA | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| C | Mouse 1 1:100 | Mouse 2 1:100 | Mouse 3 1:100 | Mouse 4 1:100 | Mouse 5 1:100 | Mouse 6 1:100 | Mouse 7 1:100 | Mouse 8 1:100 | Mouse 9 1:100 | Mouse 1 01:100 | Mouse 1 11:100 | Mouse 1 21:100 |
| D | Mouse 1 1:200 | Mouse 2 1:200 | Mouse 3 1:200 | Mouse 4 1:200 | Mouse 5 1:200 | Mouse 6 1:200 | Mouse 7 1:200 | Mouse 8 1:200 | Mouse 9 1:200 | Mouse 101:200 | Mouse 111:200 | Mouse 121:200 |
| E | Mouse 1 1:400 | Mouse 2 1:400 | Mouse 3 1:400 | Mouse 4 1:400 | Mouse 5 1:400 | Mouse 6 1:400 | Mouse 7 1:400 | Mouse 8 1:400 | Mouse 9 1:400 | Mouse 101:400 | Mouse 111:400 | Mouse 121:400 |
| F | Mouse 1 1:800 | Mouse 2 1:800 | Mouse 3 1:800 | Mouse 4 1:800 | Mouse 5 1:800 | Mouse 6 1:800 | Mouse 7 1:800 | Mouse 8 1:800 | Mouse 9 1:800 | Mouse 101:800 | Mouse 111:800 | Mouse 121:800 |
| G | Mouse 1 1:1600 | Mouse 2 1:1600 | Mouse 3 1:1600 | Mouse 4 1:1600 | Mouse 5 1:1600 | Mouse 6 1:1600 | Mouse 7 1:1600 | Mouse 8 1:1600 | Mouse 9 1:1600 | Mouse 10 | Mouse 11 | Mouse 12 |
| H | Mouse 1 1:3200 | Mouse 2 1:3200 | Mouse 3 1:3200 | Mouse 4 1:3200 | Mouse 5 1:3200 | Mouse 6 1:3200 | Mouse 7 1:3200 | Mouse 8 1:3200 | Mouse 9 1:3200 | Mouse 10 | Mouse 11 | Mouse 12 |

Figure 5:
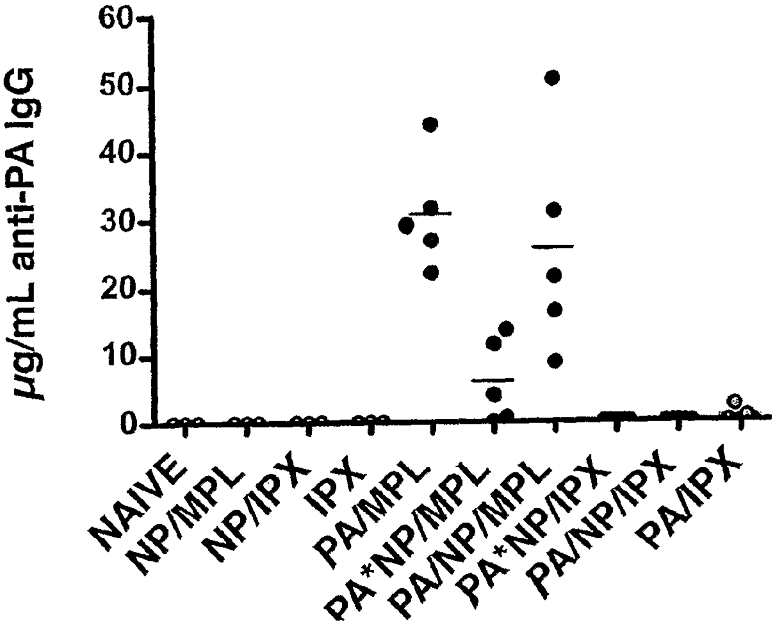
FIG. 5 shows the anti-PA IgG response measured at Week 3 (Example 3).

Antibody responses: Serum drawn prior to the initial vaccination showed no measurable recognition of PA (data not shown). Serum anti-PA responses were measured in mice three weeks post immunization, immediately prior to the boost. Mice receiving PA/MPL (delivered IP, no NP) had the greatest mean anti-PA responses in their sera at 31 μg/ml, with values ranging from 22 to 44 μg/ml. The mean response of PA/NP/MPL (free PA mixed with but not bound to NP, IP delivery) mice was statistically similar at 26 μg/ml (unpaired t-test, $p>0.05$), with values ranging from 9-51 μg/ml. Four of the five mice receiving PA*NP/MPL (PA bound to NPs delivered IP) had measurable anti-PA IgG levels (range 0 to 14 μg/ml), but the group mean response was 6 μg/ml IgG, which was significantly lower than the other two PA-containing vaccines delivered IP ($p<0.05$, FIG. 5). Two out of five mice receiving PA/IPX intranasally responded to nasally delivered PA. None of the control mice (Nave, NP/MPL, NP/IPX or IPX treatments) had measurable anti-PA responses, as expected.

Figure 6:
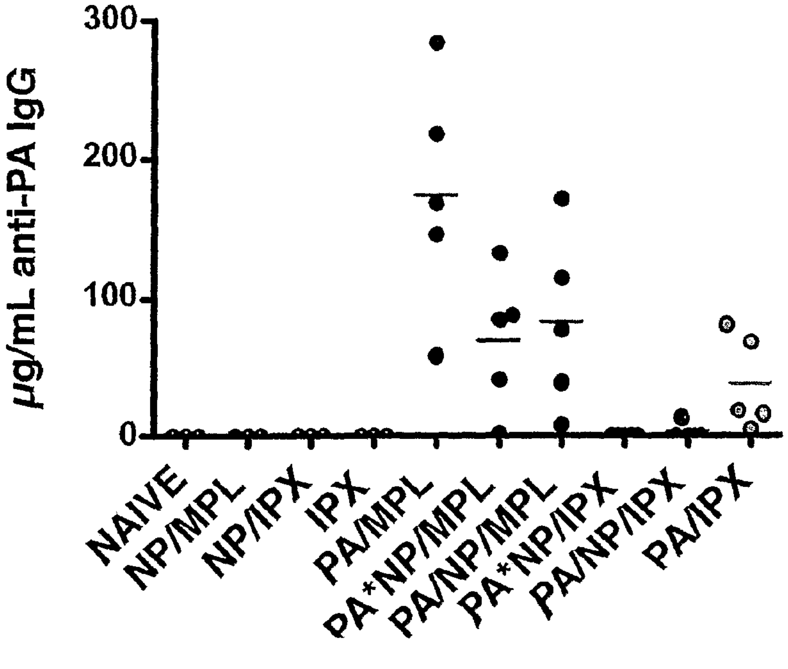
FIG. 6 shows the anti-PA IgG response measured at Week 8 (Example 3).

Results from eight week serum samples (five weeks following the boost) are shown in FIG. 6. Mice receiving PA/MPL (no NP, IP delivery) had the greatest seral anti-PA IgG responses (range of 58-284 μg/ml, mean of 175 μg/ml). The increase in mean response by PA/MPL mice compared to PA/NP/MPL mice approached statistical significance ($p<0.08$). PA/NP/MPL mice responded with values ranging from 8-172 μg/ml anti-PA IgG, with a treatment mean of 82 μg/ml. Mice receiving PA bound to NP via IP delivery (PA*NP/MPL) had responses lower than those of PA/MPL mice ($p<0.05$), but similar to those receiving the same NPs, but with unbound PA ($p>0.05$). Values for the PA*NP/MPL mice ranged from 3 μg/ml to 132 μg/ml with a mean value of 70 μg/ml.

At eight weeks, mice receiving PA/IPX intranasally had a mean seral anti-PA IgG response of 37 μg/ml (range of 4-49 μg/ml). This response was statistically similar to both PA/NP treatments, but less than PA/MPL ($p<0.05$). One mouse receiving PA/NP/IPX had measurable sera response of 13 μg/ml, however none of the others in that treatment had positive responses.

Nanoparticle effects on immune responses: His-binding NP approach of delivering an antigen did not appear advantageous. In fact, the NP inhibited anti-PA serum IgG.

Example 4

Intranasal Immunization with Multiple Anthrax Peptides

Protocol: Female Balb/c mice, 8 weeks old, were immunized on Day 0, 14, and 28. Serum samples were collected on days 0, 28, and 56. IN immunizations were in a total volume of 10 μl, and each contained 5 μg IPX50. For IN immunizations, a 5 μl/nostril bolus was delivered to each nare after lightly anesthetizing the mouse via isofluorine to effect.

Vaccine formulation: Adjuvants were added to vaccines at 5 μl/dose immediately prior to use. PA was administered at 10 μg/dose; Capsular 10-mer at 10 μg/dose; Capsule PGA at 10 μg/dose. IPX50 was obtained from Edwin V. Oaks (WRAIR). IPX50 was stored at −80° C. until immediately prior to use and thawed on ice. Adjuvants were added to PA at 5 μl/dose immediately prior to use. PA conjugates were made according to the method of Schneerson et al. (Proc Natl Acad Sci USA. 2003 Jul. 22; 100(15):8945-50. Epub 2003 Jul. 11). Vaccines formulated with cholera toxin (CT) contained 1 microgram CT.

Adjuvants: IPX50 is an ion-exchange chromatography fraction of a water extract isolated from Shigella bacteria containing the Shigella invasion complex. CT is cholera toxin.

Treatment groups: Treatment groups are shown in Tables 10 and 11.

Sampling: Serum samples were collected on days 0, 28, and 56.

Serum ELISA: Serum anti-PA and anti-Capsule IgG were measured by ELISA and the amount of IgG to each antigen was interpolated from standard curves generated in parallel as described above.

Antibody responses: Serum drawn prior to the initial vaccination showed no measurable recognition of PA (data not shown).

Figure 7:
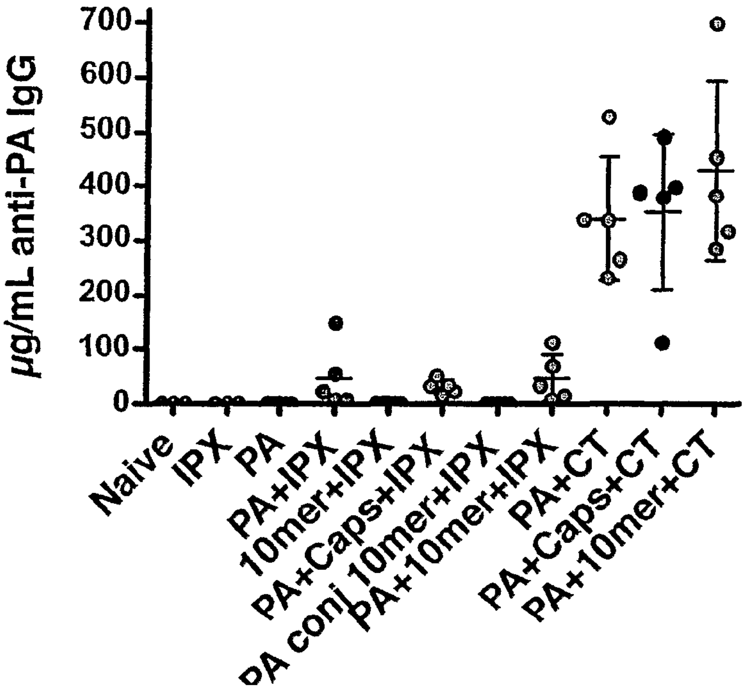
FIG. 7 shows the anti-PA IgG response measured at Week 8 (Example 4).

Serum anti-PA responses were measured in mice 8 weeks post immunization (Table 10, FIG. 7). Mice receiving PA with or without Capsule or the Capsule 10-mer with CT had mean anti-PA IgG responses ranging from 340-428 U/mL. Mice who received PA with IPX50 had measurable anti-PA IgG but the mean were responses ranged from 30-48 U/mL and some mice in each of these groups had no measurable response. The presence of the capsule or capsule 10-mer in these animals appeared to have no effect on the anti-PA response in mice receiving formulations with IPX50 or CT.

TABLE 10

| | Anti-PA IgG | | |
|---|---|---|---|
| Group | Treatment | Mean, U/mL | Standard Deviation |
| 1 | Naive | 0.0 | 0.0 |
| 2 | PA | 0.0 | 0.0 |
| 3 | IPX | 0.0 | 0.0 |

TABLE 10-continued

| Anti-PA IgG | | | |
|---|---|---|---|
| Group | Treatment | Mean, U/mL | Standard Deviation |
| 4 | PA + IPX | 48.1 | 59.2 |
| 5 | 10mer + IPX | 0.0 | 0.0 |
| 6 | PA + Caps + IPX | 30.7 | 13.5 |
| 7 | PA conj 10mer + IPX | 0.5 | 1.0 |
| 8 | PA + 10mer + IPX | 47.4 | 44.0 |
| 9 | PA + CT | 340.6 | 114.2 |
| 10 | PA + Caps + CT | 353.4 | 142.3 |
| 11 | PA + 10mer + CT | 428.1 | 163.0 |

Figure 8:
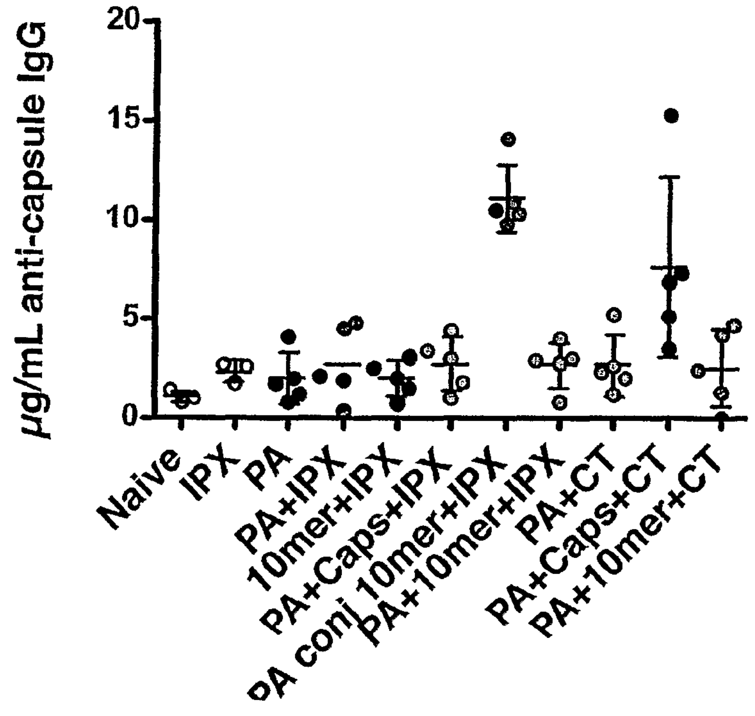
FIG. 8 shows the anti-Capsule IgG response measured at Week 8 (Example 4)

In contrast, formulations with CT did not uniformly enhance the anti-capsule IgG response (FIG. 8). The greatest responses were observed in mice receiving PA+Caps+CT but the response within the group was variable. And the responses of mice receiving PA+10-mer+CT on average were similar to mice receiving PA+CT. The most uniform and consistent anti-Capsule response in comparison to the other groups was observed in mice receiving PAconj10-mer+IPX50. The mean of 11.2 U/mL for this group exceeded the PA+Caps+CT. Furthermore, all of the mice receive PAconj10-mer+IPX50 exceeded the responses observed in 4/5 mice in the PA+Caps+group.

TABLE 11

| Anti-Capsule IgG | | | |
|---|---|---|---|
| Group | Treatment | Mean, U/mL | Standard Deviation |
| 1 | Naive | 1.1 | 0.3 |
| 2 | PA | 2.0 | 1.3 |
| 3 | IPX | 2.4 | 0.5 |
| 4 | PA + IPX | 2.8 | 1.9 |
| 5 | 10mer + IPX | 2.0 | 0.9 |
| 6 | PA + Caps + IPX | 2.7 | 1.3 |
| 7 | PA conj 10mer + IPX | 11.2 | 1.7 |
| 8 | PA + 10mer + IPX | 2.7 | 1.2 |
| 9 | PA + CT | 2.7 | 1.5 |
| 10 | PA + Caps + CT | 7.7 | 4.6 |
| 11 | PA + 10mer + CT | 2.5 | 2.0 |

Example 5

Intranasal immunization of Rabbits with PA and Capsule Antigens Elicit Antigen-Specific Serum IgG and Protects Against Aerosol Challenge with Virulent Anthrax In this experiment, we tested the protective abilities of a vaccine in a recognized model of human inhalational anthrax. The vaccine formulations tested are shown in Table 12. PA was obtained from List Biochemical, MPL-AF (monophosphoryl lipid-A, aqueous formula) from Corixa, and chitosan glutamate from West Pharmaceutical Services (Nottingham, UK). Chitosan was included in some formulations as it as been shown to have mucoadhesive properties. The poly(γ-D-glutamic acid) peptide/PA conjugate described above was used here also at a dose of 90 μg, which represented approximately 18 μg of the capsule peptide. Unconjugated PA was also included in vaccines containing conjugate to ensure that PA responses could be stimulated, as previous results suggested that PA epitopes might be altered by the conjugation process. Previous experiments had indicated that intranasal immunization of rabbits with 90 μg PA in liquid formulations gave measurable anti-PA responses in most rabbits, thus 90 μg PA dosages were utilized here also. MPL was included as an adjuvant at 25 μg/dose, and in some formulations chitosan was included as a mucoadhesive. Dry powder vaccines were formulated by West Pharmaceuticals Services and loaded into Valois Monopowder single-use nasal administration devices. Dry powder vaccines were stored at 4° C. until use. Each device contained 11 mg of powder, and delivery was calculated to be 10 mg when the plunger was depressed, with one-half dosage of vaccine delivered in the 10 mg. Two nasal administration devices were used for each rabbit (one for each nostril) that received the dry powder formulations. Liquid vaccine formulations were compounded immediately prior to use, and were administered intranasally to rabbits using MAD (Mucosal Administration Device) sprayers from Wolfe-Tory Medical, Inc. (Salt Lake City, Utah) in a total volume of 200 μl, or via single intramuscular injection of volume 100 μl. The intranasal vaccination was divided equally between both nostrils for each rabbit. For all vaccine formulations, animals were immunized on days 0 and 28 under firm restraint, but without anesthesia. Serum samples were collected prior to the first immunization (day 0), and again on day 28 (week 4, prior to the booster immunization) and on day 56 (week 8). Serum was analyzed by ELISA for antigen-specific antibody responses, and levels of PA-specific IgG were calculated from a standard curve generated with calibrated immune rabbit sera. The ELISA results were statistically analyzed by t-test comparison of pairs of treatment means, with differences considered significant if $p<0.05$.

TABLE 12

| Intranasal vaccine formulations for Example 5 | | | | | |
|---|---|---|---|---|---|
| Grp. | Treatment | Short name | Form | Route | Rabbit No. |
| D1 | Negative control dry powder | Neg | Powder | intranasal | 5 |
| D3 | PA + MPL + Chitosan + Conjugate | PA/MPL/Chito/Conj | Powder | intranasal | 10 |
| D5 | PA + MPL + Chitosan + 10-mer | PA/MPL/Chito/10-mer | Powder | intranasal | 10 |
| D6 | PA + MPL + Conjugate | PA/MPL/Conj | Powder | intranasal | 10 |
| L8 | PA + MPL + Conjugate | PA/MPL/Conj (L) | Liquid | intranasal | 10 |
| L10 | PA + MPL | PA/MPL (L, i.m.) | Liquid | intramuscular | 10 |

Figure 9:
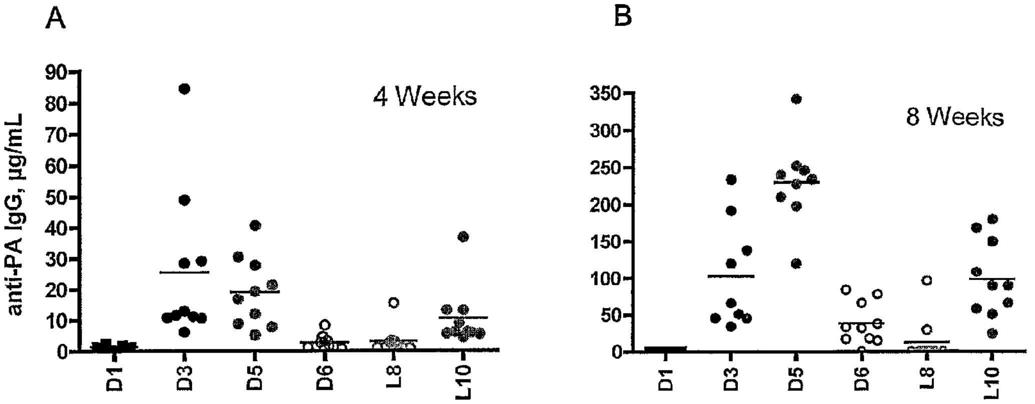
FIG. 9 shows the PA-specific serum antibody responses in rabbits at 4 weeks (A) and 8 weeks (B) after the initial immunization (Example 4). Note the different scale for the Y axis at the different time points. Each individual rabbit is indicated by a circle, and mean values for each treatment are indicated by bars. Actual anti-PA IgG values were calculated based upon a standard curve created from calibrated rabbit sera that is hyper-immune to PA, and thus reflect actual μg/mL of anti-PA IgG.

Serum levels of PA-specific IgG are shown in FIG. 9. 4 week serum samples revealed that the dry powder vaccine containing both PA and chitosan (D3, D5) as well as the intramuscular liquid formulation (L10) were able to elicit statistically significant antibody levels 4 weeks following a single intranasal immunization ($p<0.05$, Table 13). A second immunization boosted serum IgG responses against PA to even greater levels, with all PA containing vaccines, except for the intranasal liquid formulation L8, inducing significant levels of antibodies at 8 weeks ($p<0.05$). The mean PA-specific IgG levels in serum varied between the responding groups, with the most robust responses measured in rabbits immunized with PA in combination with MPL, chitosan, and the free capsule 10-mer peptide ($p<0.001$). D3 (103 μg/mL) and L10 (99 μg/mL) induced lower, but still quite impressive anti-PA responses. Finally, the dry powder formulation containing PA and MPL, but no chitosan, elicited much lower, albeit noteworthy anti-PA responses (38 μg/mL), although the same formulation in liquid form delivered intranasally did not result in statistically significant responses.

TABLE 13

Serum anti-PA IgG levels at 4 and 8 weeks after the initial immunization.

| | μg/mL ± S.D. | |
|---|---|---|
| Treatment | 4 week | 8 week |
| Negative control dry powder | $1 \pm 0.7^{a}$ | $0 + 0^{a}$ |
| PA + MPL + Chitosan + Conjugate | $26 \pm 25^{b}$ | $103 \pm 73^{b}$ |
| PA + MPL + Chitosan + 10mer | $19 \pm 11^{b,c}$ | $230 \pm 58^{c}$ |
| PA + MPL + Conjugate | $3 \pm 2^{a,c}$ | $38 \pm 29^{d}$ |
| PA + MPL + Conjugate | $3 \pm 4^{a}$ | $13 \pm 31^{a,d}$ |
| PA + MPL, intramuscular | $11 \pm 10^{b,c}$ | $99 \pm 53^{b}$ |

[a,b,c]Different letters within superscripts within a time point indicate statistical difference, $p < 0.05$.

Figure 10:
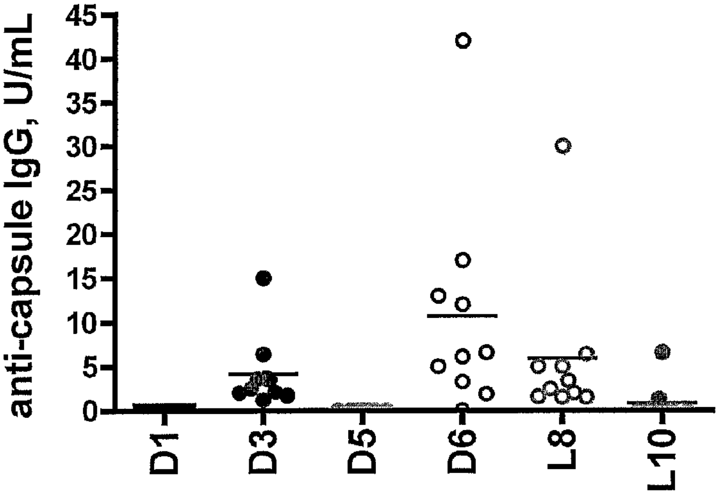
FIG. 10 shows serum anti-capsule IgG responses in rabbits at 8 weeks after initial immunization (4 weeks following the boost). Each individual rabbit is indicated by a circle. Mean values for each treatment are indicated by bars. The capture antigen was x μg/well of unconjugated poly(γ-D-glutamic acid) 10-mer peptide (Linker-(γ-D-Glu)$_9$-D-Glu-OH) (SEQ ID NO:1). Response values were interpolated from a standard curve generated with rabbit IgG, and values are expressed as units/mL. One unit (U) approximates 1 μg.

There were no anti-capsule responses identified in the 4 week serum samples (data not shown), although all vaccines containing the capsule peptide conjugate induced similar, statistically significant anti-capsule IgG levels in the 8 week serum samples (FIG. 10). The free 10-mer peptide was included in formulation D5 under the hypothesis that the highly-positive charged chitosan might bind to the negatively charged peptide and present it to immune effectors cells in a manner similar to conjugation to a protein. No anti-capsule IgG responses were observed in any rabbits immunized with D5, the free peptide containing formulation, signifying that conjugation of the capsule peptide to a carrier protein can increase capsule-specific responses.

We tested the protective efficacy of some of the vaccines. 6 or 7 rabbits selected from treatment groups D3, D5, D6 and L8 along with all 5 of the D1 rabbits were transported to the Battelle Medical Research & Evaluation Facility (West Jefferson, Ohio) 10 weeks after the initial immunization (6 weeks after the booster vaccination). After a week of quarantine, rabbits were subjected to aerosol challenge with approximately 250 $LD_{50}$ of Ames *B. anthracis* spores delivered via a muzzle-only inhalation exposure chamber. The rabbits were then observed twice daily for morbidity (anorexia) and death. Observations were recorded for 14 days following the challenge. Surviving rabbits were then euthanized following collection of a convalescent serum sample. Serum samples were analyzed for IgG responses recognizing PA, Lethal Factor (LF) and capsule and compared to the 8 week responses to determine the extent of infection experienced by individual rabbits.

Four out of five rabbits immunized with the negative control D1 formulation succumbed to anthrax during the post-challenge period, and the fifth rabbit appeared ill and ceased eating for several days prior to termination of the experiment 14 days post-challenge. All of the rabbits immunized with the other vaccine formulations were protected from death and appeared healthy throughout the experiment. All rabbits immunized with vaccines D3, D5 or D6 survived the aerosol challenge, but differences in morbidity between vaccine groups were observed (Table 15). Only rabbits immunized with the PA+PA-Conj (D3) appeared normal throughout the post-challenge observation period (14d), while all rabbits that received PA with free peptide (D5) were ill at various times as evidenced by a failure to eat normally. Since the D5 rabbits had much a higher mean serum anti-PA IgG level (236 μg/mL) than the group vaccinated with D3 (127 μg/mL), lack of morbidity/anorexia was unrelated to serum levels of anti-PA IgG. The negative control rabbit that survived the challenge received a lower inhaled spore dose (183 $LD_{50}$, Table 15), which perhaps allowed it to survive. However, it did exhibit anorexia, suggesting that it had an infection.

Figure 11:
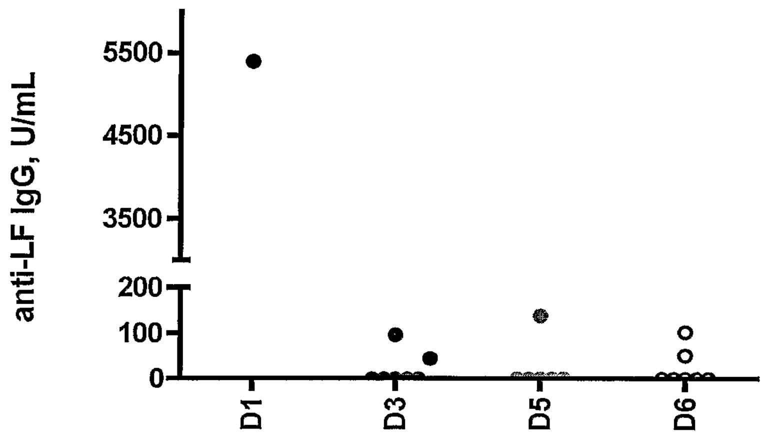
FIG. 11 shows convalescent serum anti-lethal factor (LF) IgG responses in surviving rabbits 14 days post challenge. Each individual rabbit is indicated by a circle. Response values were interpolated from a standard curve generated with rabbit IgG, and values are expressed as units/mL. One unit (U) approximates 1 μg.

To further examine the extent of protection afforded by vaccination, we measured anti-lethal factor (LF) IgG levels in those rabbits that survived challenge. We reasoned that if challenged animals did experience an actual anthrax infection, they would mount a measurable serum response against the secreted LF. None of the surviving rabbits had measurable levels of anti-LF IgG in their serum two weeks prior to challenge (data not shown), thus any LF antibodies detected in convalescent sera 14 days after challenge (FIG. 11, Table 15) must have arisen as the result of an active infection. The surviving negative control (D1) rabbit had an extremely high level of anti-LF IgG in its serum 14 days post-challenge relative to the other survivors (5400 U/mL), indicating that it experienced an active anthrax infection. A few individuals in the other immunization groups (2/7 for D3, 1/6 for D5, and 2/7 for D6) also had measurable LF levels following challenge (44 to 138 U/mL), indicating that they also suffered an active infection. However, the levels measured were less than one-tenth that found in the negative control immunized with D1, confirming that intranasal immunization with the dry powder, PA-containing formulations was able to confer substantial protection, and often sterile immunity, against the aerosol challenge.

Example 6

Intranasal Immunization with PA and Capsule Conjugates Elicits Strong Antigen-Specific T-Cell Responses The ability of PA and the PA-capsule peptide conjugate to raise antigen-specific lymphocytes was evaluated. BALB/c mice were immunized with the PA/10-mer peptide conjugate formulated with cholera toxin (CT) as an adjuvant. The first group was vaccinated intranasally with 10 mg of conjugate+1 mg CT, while the second group was vaccinated intraperitoneally with 25 mg conjugate+1 mg CT. Fourteen days following immunization, mice were euthanized, the spleens were aseptically harvested, pooled by group, and a single-cell suspension of splenocytes prepared in RPMI-1640-10% FBS. $2\times10^{5}$ cells/well were plated into 96-well plates for in vitro restimulation and the following antigens added to the wells in varying concentrations for evaluation of T-cell reactivity: 10-mer capsule peptide conjugated to bovine serum albumin (Pep10-BSA), unconjugated BSA as a control, and *B. anthracis* protective antigen (PA). The cells were then incubated for 5 days at 37° C., during which culture supernatants were harvested for cytokine evaluation using a multiplex assay (Luminex). On day 5, cultures were also assayed for lymphocyte proliferation by measuring BrdU incorporation into the DNA of the dividing cells (Cell Proliferation ELISA, Roche Applied Sciences, Indianapolis, Ind.)

Figure 12:
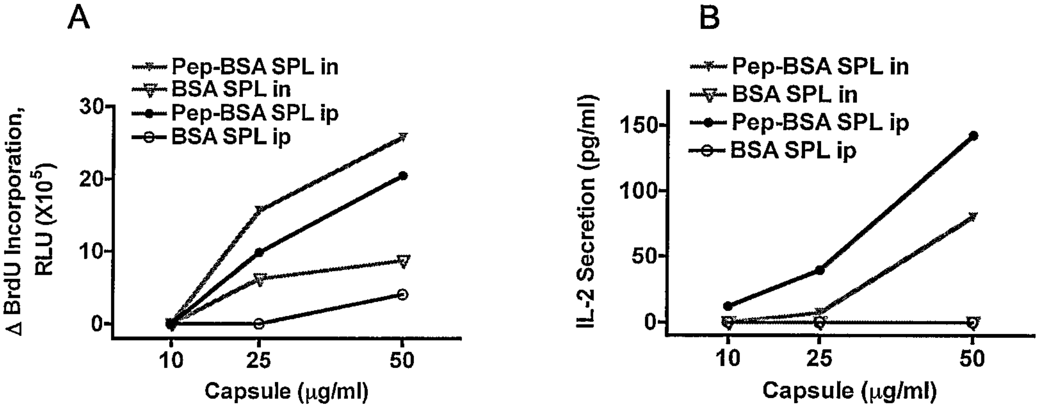
FIG. 12 shows the in vitro capsule peptide-specific responses of splenocytes from BALB/c mice immunized with the PA-peptide 10-mer conjugate. Cultures were restimulated with the capsule 10-mer peptide conjugated to BSA in order to ensure that measured effects were due to the capsule peptide. Panel A shows proliferation as measured by BrdU incorporation. Panel B shows IL-2 secretion into the culture medium.

FIG. 12A shows this in vitro proliferative response to capsule peptide following the in vivo immunization. Restimulation was conducted with the 10-mer peptide conjugated to an irrelevant carrier molecule (BSA) in order to ensure that the response was capsule-specific. These data demonstrate that immunized mice are able to mount a T-cell response specific to the capsule peptide following either an intranasal or an intraperitoneal immunization. No response to unconjugated BSA in the negative control cultures was observed, demonstrating that stimulation was not due to the presence of BSA. IL-2 was also detected in the supernatants harvested from the Pep10-BSA restimulated cultures (FIG. 12B), although not in supernatants from cultures restimulated with unconjugated BSA. Thus, capsule peptide-specific T-cells were indeed activated in these cultures. The route of immunization, intranasal versus intraperitoneal, did not appear to make a significant difference in terms of the magnitude of the response. Additionally, the presence of antigen-reactive T-cells in the spleen following an intranasal immunization is strong evidence that intranasal priming can ultimately result in a systemic immune response. In vitro restimulation using unconjugated PA also demonstrated that PA-specific T-cells are generated following immunization with the Pep10-PA conjugate, and that the conjugation reaction did not appear to alter the T-cell reactivity of PA (data not shown).

Example 7

Intranasal Immunization of Rabbits with Plasmids Encoding *Bacillus anthracis* Toxin Antigens Elicits Antigen-Specific Responses in Serum Female New Zealand White rabbits (12 weeks of age) were intranasally immunized on days 0, 28 and 56 with the formulations shown in Table 14. Serum was collected prior to the start of the experiment and again on days 28, 56 (prior to immunizations) and 84. Vaccine formulations were compounded immediately prior to use, and were administered intranasally to rabbits using a micropipettor in a total volume of 50 μl (25 μl/naris). The intranasal vaccination was divided equally between both nostrils for each rabbit.

TABLE 14

Intranasal DNA vaccine formulations.

| Rabbits per Group | Plasmids | Adjuvant | Short name | μg DNA per rabbit |
|---|---|---|---|---|
| 5 | None (Saline) | None | Saline | 0 |
| 5 | $pPA_{63} + pLF_4$ | None | DNA | 100 |
| | | | | 100 |
| 7 | $pPA_{63} + pLF_4$ | PCCE | DNA/PCCE | 100 |
| | | | | 100 |
| 7 | $pPA_{63} + pLF_4$ | IPX24 | DNA/IPX24 | 100 |
| | | | | 100 |
| 7 | $pPA_{63} + pLF_4$ | IPX24 + PCCE | DNA/IPX24/PCCE | 100 |
| | | | | 100 |
| 7 | $pPA_{63} + pLF_4$ | IPX50 | DNA/IPX50 | 100 |
| | | | | 100 |
| 7 | $pPA_{63} + pLF_4$ | IPX50 + PCCE | DNA/IPX50/PCCE | 100 |
| | | | | 100 |

pPA63 = plasmid encoding residues 175-764 (146-735 without leader sequence) of *B. anthracis* Protective Antigen pLF4 = plasmid encoding the NH2-terminal residues 10-254 of *B. anthracis* Lethal Factor IPX24 = Invaplex 24, a water extract of *Shigella flexneri* with adjuvant activities. 24 designates the elution fraction during purification.

IPX50 = Invaplex 50, a water extract of *Shigella flexneri* with adjuvant activities. 50 designates the elution fraction during purification.

PCCE = soya phosphatidylcholine + sodium cholate + ethanol, a mixture that has been shown to augment antigen-specific responses in intranasal vaccines For all vaccine formulations, animals were immunized on days 0 and 28 under firm restraint, but without anesthesia. Serum was analyzed by ELISA for antigen-specific antibody responses, and levels of LF-specific or PA-specific IgG were calculated from a standard curve generated with rabbit IgG. The ELISA results were statistically analyzed byt-test comparison of pairs of treatment means.

Figure 13:
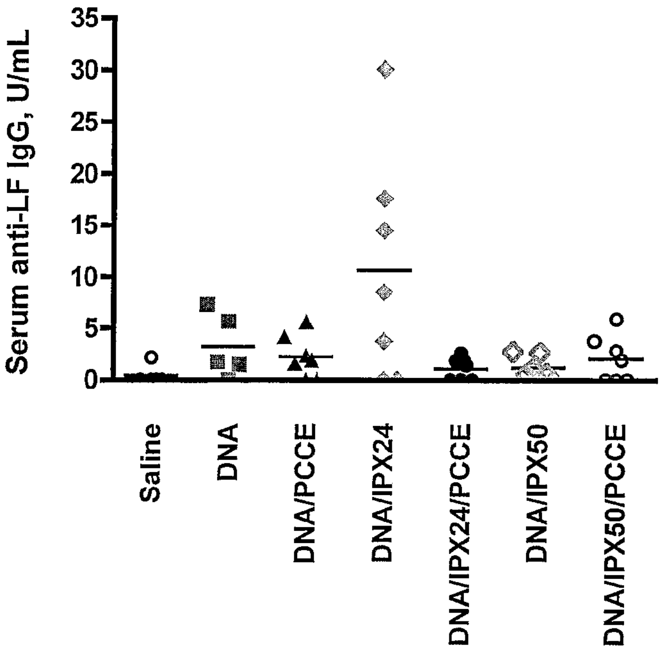
FIG. 13 shows the LF-specific responses in the serum of rabbits intranasally immunized with plasmids encoding fragments of PA and LF. Serum was collected at 12 weeks (day 84), which was 4 weeks following the final immunization. Each individual rabbit is indicated by a symbol, and mean values for each treatment are indicated by bars. The standard curve was created from rabbit IgG, thus repsonses are indicated in U/mL, with 1 U approximating 1 μg.

LF-specific responses are shown in FIG. 13. The highest responses were elicited from the group that received the plasmid expression vectors formulated with the mucosal adjuvant Invaplex 24 (DNA/IPX24). In this treatment group, 5 of 7 animals produced measurable, antigen-specific IgG levels with significant responses by 8 weeks after only 2 vaccinations (mean of 6 U/mL, range of 0-13 U/mL). By day 84 (after the 3rd immunization on day 56) mean serum IgG levels in DNA/IPX24 rabbits was 12 U/mL (range 0-30 U/mL), which was significantly different than the saline vaccinated group ($p<0.07$). These data suggest that Invaplex 24 enhanced the efficacy of nasal DNA vaccination in rabbits. In contrast, rabbits that received Invaplex 50 (DNA/IPX50) responded no better (mean 1 U/mL at 12 weeks, range 0-6 U/mL) than the group that was vaccinated with DNA alone (mean 3 u/mL at 12 weeks, range 0-6 U/mL). PCCE alone failed to bolster IgG levels (DNA/PCCE, mean 2 U/ml at 12 weeks, range 0-6 U/mL), and when co-administered with Invaplex 24 appeared to counteract the effects imparted by Invaplex 24 (DNA/IPX24/PCCE, mean 2 U/mL at 12 weeks, range 0-3 U/mL). PCCE co-administered with Invaplex 50 had little effect on IgG responses, with the exception of a single rabbit (DNA/IPX50/PCCE, mean 2 U/mL at 12 weeks, range 0-6 U/mL).

Figure 14:
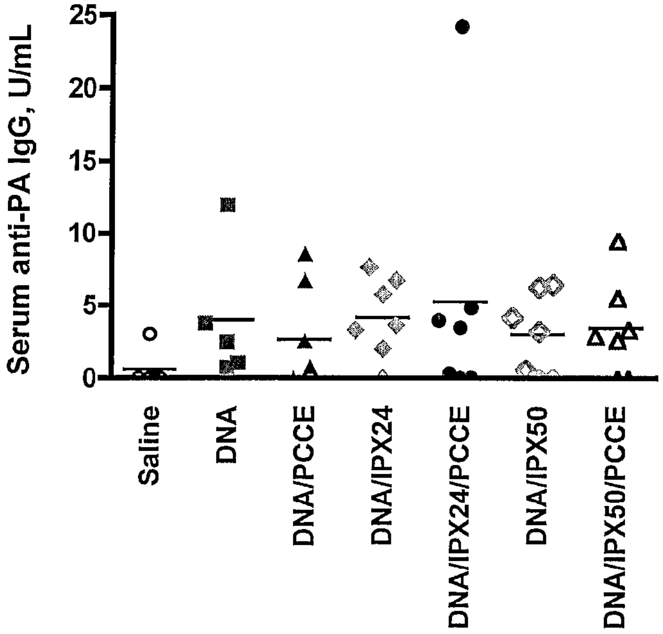
FIG. 14 shows the PA-specific responses in the serum of rabbits intranasally immunized with plasmids encoding fragments of PA and LF. Serum was collected at 12 weeks (day 84), which was 4 weeks following the final immunization. Each individual rabbit is indicated by a symbol, and mean values for each treatment are indicated by bars. The standard curve was created from rabbit IgG, thus responses are indicated in U/mL, with 1 U approximating 1 μg.

Serum PA-specific IgG responses at 12 weeks are shown in FIG. 14. The average responses between the treatment groups were relatively uniform, but low. Animals within the DNA/IPX24 vaccinated group tended to have more consistent responses, with 7 of 7 animals producing measurable amounts of PA-specific serum IgG (mean 3 U/mL, range 0-6 U/mL). The mean response to DNA/IPX24 was different from that of animals immunized with saline alone ($p<0.02$).

In summary, antigen specific serum antibody responses were induced to both *B. anthracis* Protective Antigen and Lethal Factor by intranasal immunization with plasmid DNA encoding fragments of these toxin components.

Example 8

Opsonization of *B. anthracis* Spores with Anti-Sera Recognizing BclA Increases Spore Uptake and Killing by Macrophages BclA is an abundant, glycosylated protein found in the exosporium of *Bacillus anthracis* spores. (Sylvestre et al. 2002. Mol Microbiol 45:169-178). 382 amino acid residues are encoded by the gene, and the central part of the protein contains a region of GXX motifs similar to what is found in mammalian collagen proteins.

Figure 15:
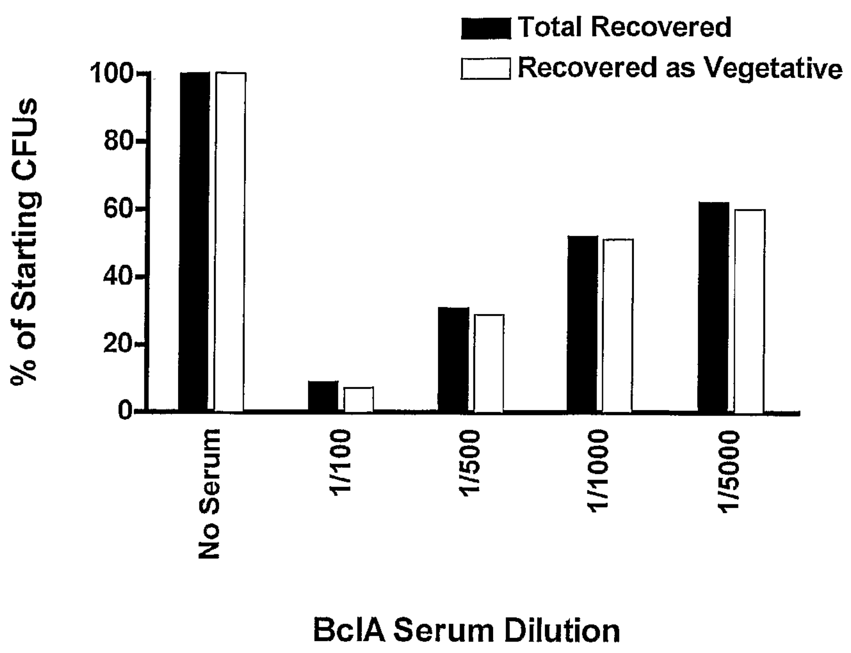
FIG. 15 shows BclA antisera enhances killing of anthrax spores by mouse macrophages. The black bars show the proportion of *B. anthracis* colony forming units (CFUs) compared to the number of CFUs added to cells as spores. The white bars indicate the proportion of starting CFUs recovered as germinated, vegetative (heat sensitive) baccili.

$1\times10^5$ J774 macrophages were plated into each well of a 6 well plate and cultured overnight in Dulbeccos Modified Medium (DMEM) with 5% fetal bovine serum (FBS). The next day, *B. anthracis* Sterne strain spores ($1\times10^5$/mL) were incubated in anti-BclA sera diluted into phagocytic uptake medium (DMEM/10% FBS/10 mM HEPES, pH 7.4) as indicated in Table 20. The spores and medium were incubated at 37° C. for 1 hour. The culture medium on the J774 cells was then replaced with 1 mL of the spore/sera/uptake medium solutions. Spores and cells were incubated at 37° C. for 1 hour and then placed on ice. The medium was harvested from each well and stored on ice, and then cells were rinsed once with 37° C. PBS (phosphate buffered saline, pH 7.4) and lysed in 1 mL/well of 2.5% saponin. The cell lysate was collected from each well and stored on ice. 100 μl of a 1/100 dilution of medium samples and lysate samples were plated on blood agar plates and incubated overnight at 37° C. The colony forming units (CFUs) were counted the following morning. The results are shown in FIG. 15.

TABLE 20

Conditions for Determining the Effects of BclA Antisera on Anthrax Spore Phagocytosis and Killing by the Mouse Macrophage Cell Line, J774

| Treatment | J774 cells/well | Sterne *B. anthracis* spores/well | Dilution of anti BclA serum |
|---|---|---|---|
| 1 | $10^5$ | $10^5$ | none |
| 2 | $10^5$ | $10^5$ | 1/100 |
| 3 | $10^5$ | $10^5$ | 1/500 |
| 4 | $10^5$ | $10^5$ | 1/1000 |
| 5 | $10^5$ | $10^5$ | 1/5000 |

The spores in all cases were very efficiently taken up by the macrophages, as evidenced by the very low numbers of heat-resistant CFUs recovered from culture medium samples after 1 hour (<2%). Essentially all of the spores added to macrophages without incubation with the BclA antisera were recovered as germinated baccili. However, killing of spores was enabled by incubation with the BclA antisera in a dose-dependent manner. Since the rate of spore uptake did not appear to be affected by the lack of or presence of BclA antisera, the decreases in the numbers of recovered viable CFUs are most likely due to killing of the spores by the macrophages. It has been recognized for some time that all phagocytosed anthrax spores do not undergo the same fate. It is well established that many of the spores germinate after being taken up by macrophages (Hanna et al. 1999. Trends Microbiol 7:180-182; Dixon et al. 1999. N Engl J Med 341:815-826), however other researchers have demonstrated a decrease in viability upon phagocytosis. (Welkos et al. 1989. Microb Pathog 7:15-35; Guidi-Rontani et al. 1999. Molecular Microbiology 31:9-17) Macrophages have a variety of receptors that are used for phagocytosis, and the use of different receptors can lead to differences in how the macrophage processes with the collected material. (Aderem et al. 1999. Annu. Rev. Immunol. 17:593-623; Hellwig et al. 2001. J. Infect. Dis. 183:871-879). Opsonizing the anthrax spore with antibody enables uptake by macrophages via the Fc receptor. Uptake by the Fc receptor, but not by other routes, has been shown to enable killing in other bacterial systems. (Aderem et al. 1999. Annu. Rev. Immunol. 17:593-623)

Example 9

Intranasal Immunization with BclA

Figure 16:
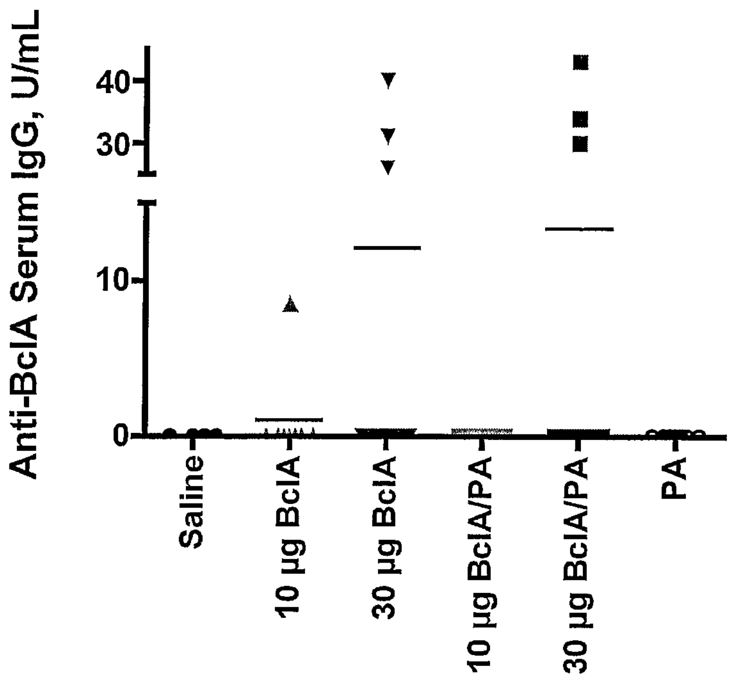
FIG. 16 shows serum antigen-specific IgG responses in mice immunized intranasally twice with BclA 21 days apart. BclA doses are indicated. PA dosages were 10 μg. All formulations except saline included 1 μg cholera toxin as an adjuvant.

Eight week old female BALB/c mice in this study were intranasally immunized on days 0 and 21 with 10 µl/mouse of the vaccine formulations shown in Table 16. Serum was collected prior to immunization on days 0 and 21, as well as on day 42. The presence of BclA-specific IgG was assayed by ELISA. Results for sera collected on day 42 are shown in FIG. 16. More mice in vaccine groups receiving 30 µg BclA/dose mounted measurable antigen-specific serum IgG responses (3 of 8 mice for both groups), while only 1 mouse immunized with 10 µg of BclA had measurable anti-BclA serum IgG antibodies on day 42 of the immunization experiment. These results demonstrate that anti-BclA responses are induced by intranasal immunization, although dosage needs to be optimized.

TABLE 16

Treatments tested

| Group | No. of mice | Treatment | Antigen amt per mouse, per dose | Adjuvant |
|---|---|---|---|---|
| 1 | 5 | None (Saline) | 0 | None |
| 2 | 8 | BclA | 10 µg | CT 1 µg |
| 3 | 8 | BclA | 30 µg | CT 1 µg |
| 4 | 8 | BclA/PA | 10/10 µg | CT 1 µg |
| 5 | 8 | BclA/PA | 30/10 µg | CT 1 µg |
| 6 | 8 | PA | 10 µg | CT 1 µg |

Example 10

Immunization with Capsule Antigen

Capsule (poly (d) Glutamic Acid) antigen from *B. anthracis* was conjugated to NP (polymerized liposome nanoparticles) or KLH. MPL was used at the manufacturer's recommended concentrations. Nanoparticles (NP) were conjugated to *B. anthracis* purified capsule with different concentrations of nanoparticles presenting 1.6 mg of capsule/dose. KLH-capsule conjugates were made using Pierce EZ Antibody Production and Purification Kit, Carboxyl Reactive, Cat. No. 77627. All mice received an estimated 20 µg capsule/mouse, with 100 µL adjuvant and 50 µL antigen for a total of 150 µL subcutaneously. Immunization groups are shown in Table 17."

TABLE 17

Capsule Conjugate Treatment Groups

| Vaccine | Short Name | Capsule dose | NP dose | Adjuvant | n |
|---|---|---|---|---|---|
| Adj only | Adj | None | None | MPL | 3 |
| JN 6-142-5[a] | NP | None | 3 mg | MPL | 3 |
| JN 6-142-1 | NPa + Caps | 20 µg | 3 mg | MPL | 5 |
| JN 6-142-2 | NPb + Caps | 20 µg | 1.4 mg | MPL | 5 |
| JN 6-142-3 | NPc + Caps | 20 µg | 0.6 mg | MPL | |
| Caps/KLH | KLH + Caps | 20 µg | None | MPL | 5 |

[a]Lot numbers

Figure 17:
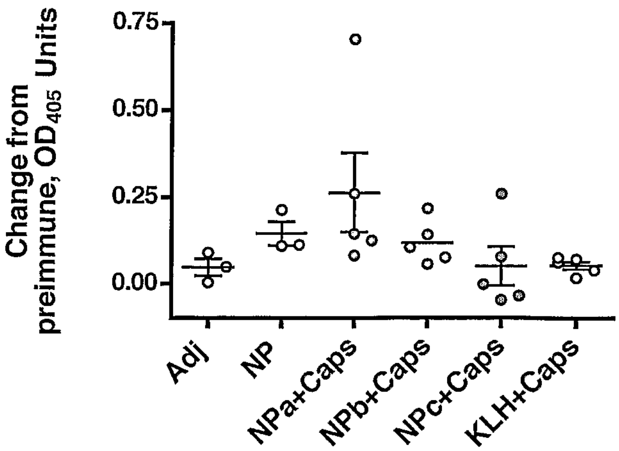
FIG. 17 shows the capsule-specific serum IgG antibody levels 2 weeks following the booster immunization with the vaccine formulations shown in Table 17.

Mice were bled and immunized on Day 0 and boosted on Day 7. Two bleeds were taken on Day 15 (1st bleed) and Day 21 (2d bleed). ELISA data was read on a Dynex Revelation plate reader. Data indicate that the highest dose of NP conjugated to capsule gave the highest titer. Results of the analysis of serum collected on day 21 are shown in FIG. 17. The lower NP doses conjugated to capsule did not induce anti-capsule responses different from those of NP alone. Conjugation of the capsule to KLH did not result in a significant antibody response.

We determined if an antigen-specific antibody responses can be induced to a 9-mer peptide (Ac-Cys-Gly-Gly-Gly-(γ-D-Glu)$_8$-D-Glu-OH) (SEQ ID NO:2) representing the *B. anthracis* capsule when presented on a nanoparticle. The adjuvant used was Gerbu Adjuvant (Gerbu Biotechnik) in all doses but the naïve mice. Nanoparticles (NP) were conjugated to single Glu amino acid residues or the 9-mer poly(D) gamma glutamic acid peptides. The immunization groups are shown in Table 18. Mice were bled and immunized on Day 0 and boosted and bled on Day 14 (1st bleed). Mice were bled on Day 21 (2d bleed), boosted on Day 28 and bled on Day 35 (3d bleed).

Figure 18:
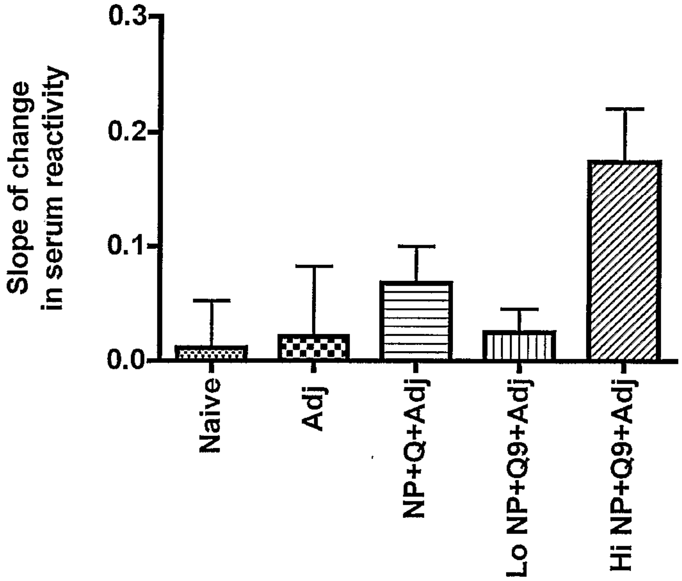
FIG. 18 The mean slopes of vaccine groups as calculated by plotting anti-capsule serum IgG $OD_{405}$ values from preimmune sera and temporal bleeds.

The changes in capsule specific serum IgG reactivity are represented in FIG. 18 as the slope of the line predicted by the changes in $OD_{405}$ over the period spanning from the preimmune bleed to the 3rd bleed 35 days later. This plotting slope allows the trends in reactivity to be visualized more easily. The greater the slope, the more steeply the line climbs, indicating greater rises in reactivity. Thus, the Hi NP+Q9+Adj vaccine induced the greatest change in serum IgG reactivity to capsule over the 35 day immunization period.

TABLE 18

Capsule Peptide Treatment Groups

| Vaccine | Short Name | Glu or $Glu_9$ dose | NP dose | Adjuvant | n |
|---|---|---|---|---|---|
| Naïve | Naïve | None | None | None | 3 |
| Adj only | Adj | None | None | Gerbu | 3 |
| JN NP 6-161-3 Glu | NP + Q + Adj | 20 µg | 2.8 mg/ml | Gerbu | 3 |
| JN NP 6-161-1 $Glu_9$ | Lo NP + Q9 + Adj | 20 µg | 0.8 mg/ml | Gerbu | 5 |
| JN NP 6-161-2 $Glu_9$ | Hi NP + Q9 + Adj | 20 µg | 2.8 mg/ml | Gerbu | 5 |

The study outlined above (Table 18) was repeated using Qiagen Immuneasy CpG adjuvant in all doses but the naïve mice. Nanoparticles were conjugated to single Glu amino acid residues or the 9-mer poly(D)gamma glutamic acid peptides. The immunization groups are shown in Table 19. Mice were immunized on Day 0 and boosted and bled on Day 14 (1st bleed). Mice were bleed on Day 21 (2nd bleed), boosted on Day 28, and bled on Day 35 (3d bleed).

TABLE 19

Capsule Peptide Treatment Groups

| Vaccine | Short Name | Glu or $Glu_9$ dose | NP dose | Adjuvant | n |
|---|---|---|---|---|---|
| Naïve | Naïve | None | None | None | 3 |
| Adj only | Adj | None | None | CpG | 3 |
| JN NP 6-161-3 Glu | NP + Q + Adj | 20 µg | 2.8 mg/ml | CpG | 3 |
| JN NP 6-161-1 $Glu_9$ | Lo NP + Q9 + Adj | 20 µg | 0.8 mg/ml | CpG | 5 |
| JN NP 6-161-2 $Glu_9$ | Hi NP + Q9 + Adj | 20 µg | 2.8 mg/ml | CpG | 5 |

Figure 19:
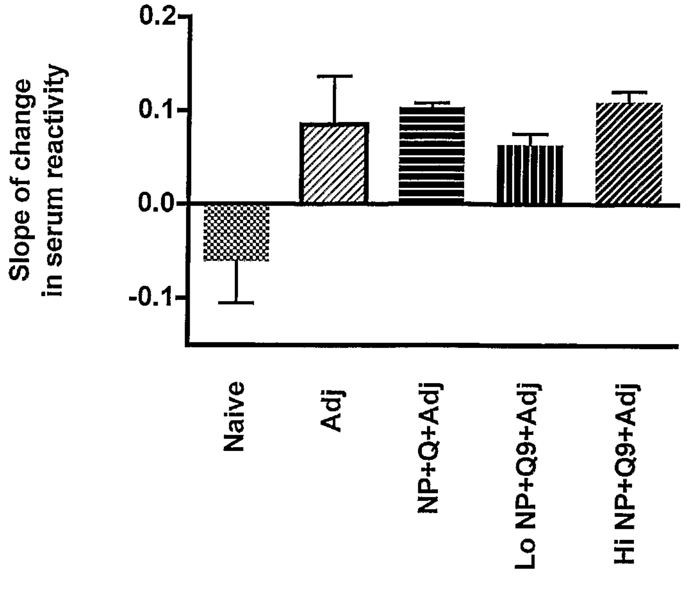
FIG. 19 shows capsule-specific serum IgG antibody levels 2 weeks following the booster immunization with the vaccine formulations shown in Table 19.

The changes in capsule specific serum IgG reactivity are represented in FIG. 19 as the slope of the line predicted by the changes in $OD_{405}$ over the period spanning from the preimmune bleed to the 3rd bleed 35 days later. Plotting slope allows the trends in reactivity to be visualized more easily. The greater the slope, the more steeply the line climbs, indicating greater rises in reactivity. In this experiment, there was not an associated increase in serum IgG reactivity to capsule over the 35 day immunization period. This in contrast to the previous experiment outlined in Table 18, where the Hi NP+Q9+Adj vaccine appeared was associated with a greater increase in reactivity than the other vaccine formulations. This apparent difference may be due to the difference in adjuvant used in the two experiments, but this has not been verified.

TABLE 15

Aerosol Challenges, Clinical Observations, and Mortality Results

| | | Inhaled | | | 8 week serum | | | 8 wk nasal wash | Post-challenge serum | |
|---|---|---|---|---|---|---|---|---|---|---|
| | ID No. | Ames $LD_{50}$ Equiv. | Clinical Observations[1] | | α-PA IgG, U/mL | α-Caps IgG, U/mL | $IC_{50}$ in TNA, dilution | α-PA IgA, U/µg total IgA | α-LF IgG, U/mL | α-PA IgG, µg/mL |
| Neg. Control | 1 | 183 | Anorexia on days 6, 7, 8, 9, 10. | Lived | 0 | 0 | 0 | BD[2] | 5,400 | 10,260 |
| | 2 | 288 | Appeared normal up to death. | Died d 4 | 0 | 0 | 0 | BD | — | — |
| | 3 | 212 | Lethargy and anorexia on day 2. | Died d 3 | 0 | 0 | 0 | BD | — | — |
| | 4 | 200 | Lethargy and anorexia on day 2. | Died d 3 | 0 | 0 | 0 | BD | — | — |
| | 5 | 276 | Anorexia on days 5, 6, and 7. Seemed to have seizures and had no stool on day 6. | Died d 7 | 0 | 0 | 0 | BD | — | — |
| PA + MPL + Chito + Conj | 6 | 289 | Appeared normal throughout. | Lived | 51 | 3 | 1019 | | 0 | 3,552 |
| | 8 | 265 | Appeared normal throughout. | Lived | 66 | 4 | 844 | BD | 96 | 1,074 |
| | 10 | 285 | Appeared normal throughout. | Lived | 120 | 2 | 1793 | BD | 0 | 900 |
| | 11 | 256 | Appeared normal throughout. | Lived | 45 | 4 | 1112 | BD | 0 | 1,650 |
| | 12 | 271 | Appeared normal throughout. | Lived | 138 | 6 | 1936 | BD | 0 | 1,428 |
| | 13 | 229 | Appeared normal throughout. | Lived | 234 | 15 | 2332 | BD | 0 | 2,598 |
| | 14 | 216 | Appeared normal throughout. | Lived | 234 | 4 | 1044 | BD | 44 | 6,180 |
| PA + MPL + Chito + free peptide | 16 | 223 | Anorexia on days 6 and 7. | Lived | 210 | 0 | 1687 | BD | 0 | 2,400 |
| | 17 | 282 | Anorexia on days 6, 7, and 8. | Lived | 246 | 0 | 1842 | BD | 0 | 1,740 |
| | 18 | 266 | Anorexia on days 0, 1, 2, 3, 6, 7, 8. Had no stool on day 6. | Lived | 252 | 0 | 1855 | BD | 138 | 4,200 |
| | 19 | 273 | Anorexia on day 7. | Lived | 342 | 0 | 2488 | 55,229 | 0 | 1,740 |
| | 20 | 232 | Anorexia on days 2, 6, 7, 8, and 10. | Lived | 234 | 0 | 2341 | BD | 0 | 2,034 |
| | 21 | 195 | Anorexia on days 6, 7, and 8. | Lived | 234 | 0 | 2855 | BD | 0 | 1,008 |
| PA + MPL + Conj | 26 | 230 | Anorexia on day 6. | Lived | 66 | 42 | 278 | BD | 102 | 11,040 |
| | 28 | 164 | Appeared normal throughout. | Lived | 78 | 5 | 327 | BD | 0 | 2,460 |
| | 29 | 263 | Appeared normal throughout. | Lived | 32 | 13 | 98 | BD | 0 | 1,368 |
| | 31 | 339 | Appeared normal throughout. | Lived | 15 | 12 | 286 | BD | 0 | 1,656 |
| | 32 | 344 | Appeared normal throughout. | Lived | 33 | 6 | 407 | 7,022 | 51 | 1,860 |

TABLE 15-continued

| Aerosol Challenges, Clinical Observations, and Mortality Results | | | | | | | | | |
|---|---|---|---|---|---|---|---|---|---|
| | Inhaled | | | 8 week serum | | | 8 wk nasal wash | Post-challenge serum | |
| ID No. | Ames $LD_{50}$ Equiv. | Clinical Observations[1] | | α-PA IgG, U/mL | α-Caps IgG, U/mL | $IC_{50}$ in TNA, dilution | α-PA IgA, U/μg total IgA | α-LF IgG, U/mL | α-PA IgG, μg/mL |
| 34 | 295 | Anorexia 0, 2, 5, 6, 7, 8, 9, 10, 13. | Lived | 84 | 7 | 459 | BD | 0 | 1,860 |
| 35 | 264 | Anorexia on days 5, 6, and 7. | Lived | 0 | 17 | 0 | 6,888 | 0 | 3,720 |

What is claimed is:

1. A dry powder immunogenic composition formulated for mucosal surface administration comprising unconjugated protective antigen (PA), chitosan, and MPL.

2. The dry powder composition of claim 1 in combination with one or more devices for administering one or more doses of said composition.

3. The dry powder composition of claim 2, wherein said one or more doses are unit doses.

4. The dry powder composition of claim 2, wherein the device is a single-use nasal administration device.

5. The composition of claim 1 in combination with a mucosal administration device.

6. The composition of claim 1, wherein the composition induces anti-PA-specific IgG serum antibodies in a subject when administered to a mucosal surface of the subject.

7. A method of inducing an immune response to anthrax in a subject, comprising administering to a mucosal surface of the subject an effective amount of the composition of claim 1.

8. The method of claim 7, wherein replication of anthrax in the subject is inhibited.

9. The method of claim 7, wherein anthrax exotoxin in the subject is neutralized.

10. The method of claim 7, wherein the immune response is a protective immune response.

11. The method of claim 7, wherein the mucosal surface is selected from the group consisting of a nasal mucosal surface and an oral mucosal surface.

12. The method of claim 7, wherein the subject has not been exposed to anthrax.

13. The method of claim 7, wherein the subject is infected with anthrax.

14. The method of claim 7, wherein the subject has been exposed to anthrax.

15. The method of claim 14, wherein the subject does not display visible signs of anorexia, lethargy and/or death as a result of exposure to anthrax.

16. The method of claim 15, wherein the subject does not display visible signs of anorexia, lethargy and/or death up to 2 weeks after anthrax exposure.

* * * * *

UNITED STATES PATENT AND TRADEMARK OFFICE

CERTIFICATE OF CORRECTION

PATENT NO. : 8,409,590 B2
APPLICATION NO. : 10/589290
DATED : April 2, 2013
INVENTOR(S) : Wimer-Mackin It is certified that error appears in the above-identified patent and that said Letters Patent is hereby corrected as shown below:

In the Specification,

Column 1, lines 13-16

Please delete “This invention was made with government support under DOD contract DAMD17-01-C-0040. The US Government may have certain rights in the invention as a result of this support.” and insert therefor --This invention was made with Government support under DAMD17-01-C-0400 awarded by the U.S. Army. The Government has certain rights in this invention.--

Signed and Sealed this
Twenty-second Day of September, 2015

Michelle K. Lee
*Director of the United States Patent and Trademark Office*